US012207692B2

(12) United States Patent
Kuniyasu

(10) Patent No.: US 12,207,692 B2
(45) Date of Patent: Jan. 28, 2025

(54) ETIQUETTE MASK

(71) Applicant: Chitosan Kowa Corporation, Tochigi (JP)

(72) Inventor: Haruko Kuniyasu, Tokyo (JP)

(73) Assignee: Chitosan Kowa Corporation, Tochigi (JP)

( * ) Notice: Subject to any disclaimer, the term of this patent is extended or adjusted under 35 U.S.C. 154(b) by 0 days.

(21) Appl. No.: 18/720,805

(22) PCT Filed: Mar. 31, 2022

(86) PCT No.: PCT/JP2022/016846
§ 371 (c)(1),
(2) Date: Jun. 17, 2024

(87) PCT Pub. No.: WO2023/157327
PCT Pub. Date: Aug. 24, 2023

(65) Prior Publication Data
US 2025/0000187 A1   Jan. 2, 2025

(30) Foreign Application Priority Data
Feb. 18, 2022   (JP) ................. 2022-023637

(51) Int. Cl.
*A41D 13/11*   (2006.01)
*A61F 9/04*    (2006.01)

(52) U.S. Cl.
CPC .......... *A41D 13/1161* (2013.01); *A61F 9/045* (2013.01)

(58) Field of Classification Search
CPC .... A41D 13/1161; A41D 13/11; A41D 13/05; A41D 13/00; A41D 13/1107; A41D 13/1169; A41D 13/1176; A41D 13/1184; A41D 13/1192; A41D 13/1218; A61F 9/045; A61F 9/04; A61F 9/06; A61F 9/065
See application file for complete search history.

(56) References Cited

FOREIGN PATENT DOCUMENTS

| JP | 3157299 U    | 2/2010  |
| JP | 2011240113 A | 12/2011 |
| JP | 3183826 U    | 5/2013  |

(Continued)

OTHER PUBLICATIONS

International Search Report, Japan Patent Office, Jun. 7, 2022.
Written Opinion International Search Authority, Japan Patent Office, Jun. 7, 2022.

*Primary Examiner* — Tarla R Patel
(74) *Attorney, Agent, or Firm* — Bay State IP, LLC

(57) ABSTRACT

The object of this disclosure is to provide an etiquette mask that contributes to consideration for those around the wearer under infectious disease control, reduces feelings of pressure and difficulty of breathing, and prevents the mouth from being seen from the outside even when it opens during napping or sleeping. The etiquette mask 2A has an upper mask part 4 that covers the eye region (eyes and their surroundings), a silk-made lower mask part 6 sewn and attached at the upper end thereof to the upper mask part 4 and covering the face below the eye region, and a rubber band 8 provided on the upper mask part 4, which serves as a wearing part to prevent the etiquette mask 2A from falling off the face. Since the lower mask part 6 only covers the face due to its own weight, there is no feeling of pressure.

4 Claims, 23 Drawing Sheets

(56) References Cited

FOREIGN PATENT DOCUMENTS

| JP | 2014033699 A | | 2/2014 |
|---|---|---|---|
| JP | 2014088650 A | * | 5/2014 |
| JP | 2016079532 A | * | 5/2016 |
| JP | 3228052 U | | 10/2020 |
| JP | 6860647 B | | 4/2021 |
| JP | 202212267 A | | 1/2022 |
| KR | 1020120102299 A | | 9/2012 |

* cited by examiner

ETIQUETTE MASK

CROSS REFERENCE TO RELATED APPLICATION

This application is for entry into the U.S. National Phase from which priority is claimed under all applicable sections of Title 35 of the United States Code including, but not limited to, Sections 120, 363, and 365(c) to International Application No. PCT/JP2022/016846 filed on Mar. 31, 2022, and which in turn claims priority under 35 USC 119 to Japanese Patent Application No. JP2022023637 filed on Feb. 18, 2022, the contents of which are incorporated by reference herein in its entirety as part of the present application.

TECHNICAL FIELD

The present invention relates to an etiquette mask that can cover the entire face during nap times and the like.

BACKGROUND ART

Conventionally, eye masks formed from light-blocking materials have been used to enhance restfulness and sleep quality during napping or sleeping. An eye mask, as the name suggests, has a shape that covers the eyes and their surroundings (refer, for example, to Patent Document 1).

RELATED ART DOCUMENTS

Patent Documents

[Patent Document 1]
U.S. Pat. No. 6,860,647

SUMMARY OF THE INVENTION

Problem to be Solved by the Invention

This type of eye mask is used in situations like taking a nap in a train or airplane, or in the resting rooms of public bathhouses, and depending on the depth of sleep, there may be cases where one unconsciously opens their mouth. While there's no need to worry about this in private settings like one's bedroom, in public places like those mentioned above, there's a risk of embarrassment or of causing discomfort to others. Also, under the current circumstances, where measures against coronavirus infections are being called for, there is concern about the spread of the virus from the nose and mouth, which are not covered by the eye mask.

Although wearing a regular mask (that covers the nose and mouth) along with the eye mask can alleviate the aforementioned concern, wearing two different items can be cumbersome, and one may forget to wear one of them. Also, both are typically used by hooking elastic cords or the like around the ears, which can cause discomfort to the ears, and depending on the person, they may feel a sense of oppression or difficulty to breathe caused by wearing the mask. Furthermore, in daily life when measures against infectious diseases like the coronavirus are no longer necessary, wearing a regular mask just to conceal an open mouth, along with an eye mask, cannot be denied to give a sense of overprotection (exaggeration), thereby making one prone to feelings of oppression or difficulty to breathe, and it may cause a factor to disturb the restfulness and sleep-enhancing which are the essential purpose of wearing the eye mask.

In addition, there may be times when one wants to refresh themselves by breathing the outside air directly, such as when feeling stifled, but taking the mask off entirely or largely shifting the mask may cause discomfort to others around the one.

The present invention has been made in view of the above points, and its purpose is to provide an etiquette mask that can conceal the mouth from external view during napping or sleeping even if the mouth is open, can reduce feelings of oppression and difficulty to breathe, and can contribute to a consideration for others surrounding one wearing the etiquette mask under infection control measures. Another objective of the present invention is to provide an etiquette mask that can achieve both of breathing outside air at any timing by partially opening with a simple operation without having to take the mask off entirely or largely shift the mask and also the observance of etiquette.

Means for Solving the Problem

In order to achieve the above objectives, the etiquette mask of the present invention (2A-2G) is characterized by comprising an upper mask portion (4) covering the eye area (14a) on the face (14), a lower mask portion (6) covering the lower side of the eye area (14a) on the face (14), and a wearing portion (8) provided on at least one of the upper mask portion (4) and the lower mask portion (6) that prevents slipping off the face (14).

With the etiquette mask (2A-2G) according to the present invention, for example, even if you unconsciously open your mouth during a nap in public places such as inside a train or an airplane, it can prevent this from being observed from the outside, thus preventing embarrassing situations or giving discomfort to others surrounding you. Also, it can contribute to the consideration for the surroundings under the countermeasures against infectious diseases such as coronavirus.

Also, the etiquette mask (2H-2K) according to the present invention is characterized by comprising a lower mask portion (58) which includes an opening (64, 68) at a position corresponding to the nose (14c) and/or mouth (14b) on the face (14), and a covering cover (62, 66, 72) which is attached to either the upper mask portion (18) or the lower mask portion (58) and can cover the opening (64,68) so as to open and close them.

With the etiquette mask (2H-2K) according to the present invention, you can refresh at any timing without giving discomfort to others surrounding you by partially opening the mouth with a simple operation of rolling up the covering cover without removing or largely shifting the entire mask, when you feel suffocated, and you can return to the state of complying with etiquette by a simple operation of lowering the rolled up covering cover.

In addition, in the above-mentioned etiquette mask (2H-2K), the opening (64) corresponding to the nose (14c) and the opening (68) corresponding to the mouth (14b) may be served by a single opening (70). This makes the forming work of the opening easier and facilitates breathing of outside air.

Also, in the above-mentioned etiquette mask (2K), the covering cover (72) may be configured to include an upper cover (72A) that covers the opening (64) corresponding to a position of the nose (14c) and a lower cover (72B) that covers the opening (68) corresponding to a position of the mouth (14b). This allows you to use the covering cover separately for breathing outside air through your nose and/or mouth, thereby enabling efficient use.

Also, in the above-mentioned etiquette mask (2K), the lower cover (72B) may be longer in the vertical direction of the face than the upper cover (72A), may be placed overlapping on the lower side of the upper cover (72A), and may include an overlapping opening (74) that overlaps the opening (64) corresponding to the nose (14c). This makes it possible to reduce the amount of roll up when breathing outside air through the nose.

Furthermore, in the above-mentioned etiquette mask (2H-2K), the covering cover (62, 66, 72) may be detachably attached. This allows you to maintain the state of breathing outside air through your nose or mouth as desired.

Also, in the above-mentioned etiquette mask (2A-2K), the lower mask part (20) may be detachably attached to the upper mask part (18). This allows for easy replacement in case the lower mask part gets dirty or when you want to change it to your preferred color or pattern.

Also, in the etiquette mask (2A-2K) as mentioned above, the lower mask part (6) may be formed with a soft fabric that deforms according to the changes in the unevenness of the face (14). This allows the mask to fit to the surface of the face by its own weight when worn on the face, making it easy to prevent observation from outside and providing sufficient consideration to the surroundings against leakage of breath.

Also, in the etiquette mask (2A-2K) as mentioned above, a gather (32) may be applied to at least part of the periphery of the lower mask part (30), and the lower mask part (30) may have a curved shape that protrudes outwardly from the face. This reduces the feeling of pressure and difficulty of breathing when wearing the etiquette mask and makes breathing easier.

Also, in the etiquette mask (2A-2K) as mentioned above, the lower mask part (20) may have a bellows configuration (26) that presents a curved shape that protrudes outwardly from the face (14) by pulling in the vertical direction of the face (14). This design can be flat before use, making it easy to store and handle, and can be shaped into a curved form that makes breathing easier and reduces feelings of pressure and difficulty of breathing with a simple pull. After use, it can easily be folded back to its original flat shape.

Also, in the etiquette mask (2A-2K) as mentioned above, the upper mask part (44) and the lower mask part (46) may be formed as a single continuous piece of the same material, and the lower mask part (46) may have a bellows configuration (48) that presents a curved shape that protrudes outwardly from the face (14) by pulling in the vertical direction of the face (14). This design allows obtaining the two functionalities from one material, reducing manufacturing costs. Moreover, it makes it possible to keep most of the etiquette mask (2) flat, saving space during storage and distribution.

Also, in the etiquette mask (2A-2K) as mentioned above, the lower mask part (52) may be formed in a cylindrical shape to be worn around the face and neck. This can prevent cooling of the back of the neck during napping, for example.

Also, in the etiquette mask (2A-2K) as mentioned above, the wearing part may be a hole (54) for hanging on the ear provided on each both sides of the lower mask part (52). This design is simpler and gives less tightening to the user, compared with a case where a rubber band (8) or the like is provided, eliminates ear pain, and can enhance restfulness and quality of sleep.

Also, in the etiquette mask (2A-2K) as mentioned above, earplugs (9) may be provided integrally with either the upper mask part (4) or the lower mask part (6). This allows you to enhance restfulness and sleep quality while reducing ambient noise, and you don't have to worry about storing the earplugs after removal.

The etiquette mask (2A-2K) of the present invention may comprise an upper mask part (44) that covers the eye part on the face, a lower mask part (46) provided integrally with the upper mask part (44) on the lower side thereof and covers the lower side of the eye part on the face, and a wearing part (8) provided on at least either one of the upper mask part (44) and the lower mask part (46) so as to prevent the etiquette mask from slipping off the face, and the upper mask part (44) and the lower mask part (46) may be formed as a single continuous piece of the same material, and the lower mask part (46) may have a bellows configuration (48) that presents a curved shape that protrudes outwardly from the face by pulling in the vertical direction of the face. This makes manufacturing easier.

The etiquette mask (2) of the present invention may also have slit-shaped openings (47, 49) provided at positions corresponding to the eye (14a) part in the upper mask part (44) and the mouth (14b) and its surrounding part in the lower mask part (46).

According to this configuration, having an opening in the upper mask part allows for a clear field of view, making it possible to perform tasks such as farming while wearing the etiquette mask. Having an opening in the lower mask part allows for drinking, or eating snacks while wearing the etiquette mask, when taking breaks during intervals of farm work, for instance. In addition, it has the effect of making the wearer's voice more audible to the outside through the opening.

Effects of the Invention

According to the present invention, it is possible to prevent observation from outside even when the mouth opens during a nap or sleep, to reduce the feeling of pressure and difficulty of breathing, and to contribute to consideration for the surroundings under infection control. Also, it is possible to achieve both of breathing outside air at any timing by partially opening the mask with a simple operation without taking the mask off entirely or largely shifting the mask and keeping the observance of etiquette.

BRIEF DESCRIPTION OF DRAWINGS

FIG. 1 A drawing showing an etiquette mask according to the first embodiment of the present invention, where

FIG. 6 A drawing showing an etiquette mask according to the third embodiment, where

FIG. 7 A drawing showing an etiquette mask according to the fourth embodiment, where

FIG. 8 A drawing showing an etiquette mask according to the fifth embodiment, where

FIG. 14 A drawing showing an etiquette mask according to the eighth embodiment, where

FIG. 20 Front views showing the etiquette mask shown in FIG. 19, where

BEST MODE FOR CARRYING OUT THE INVENTION

Hereinafter, embodiments of the present invention will be explained in detail with reference to the accompanying drawings.

First Embodiment

Figure 1A:
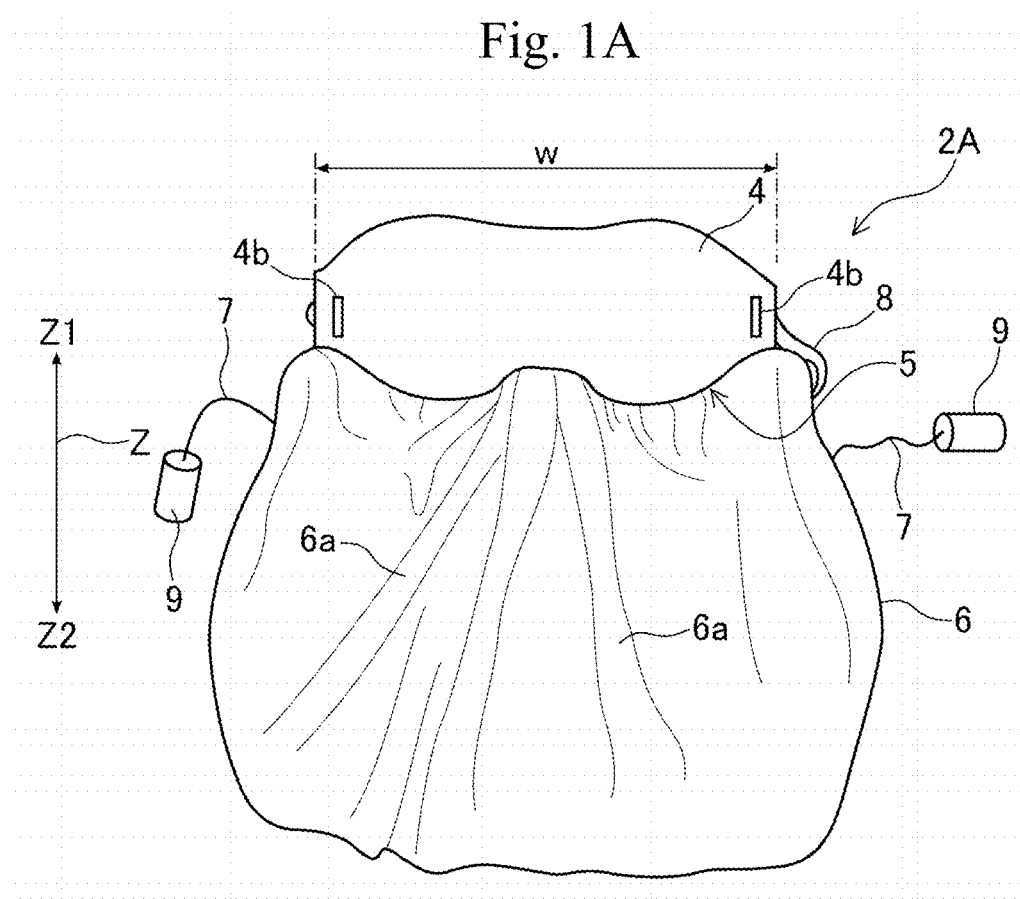
FIG. 1A is a front view.
Figure 1B:
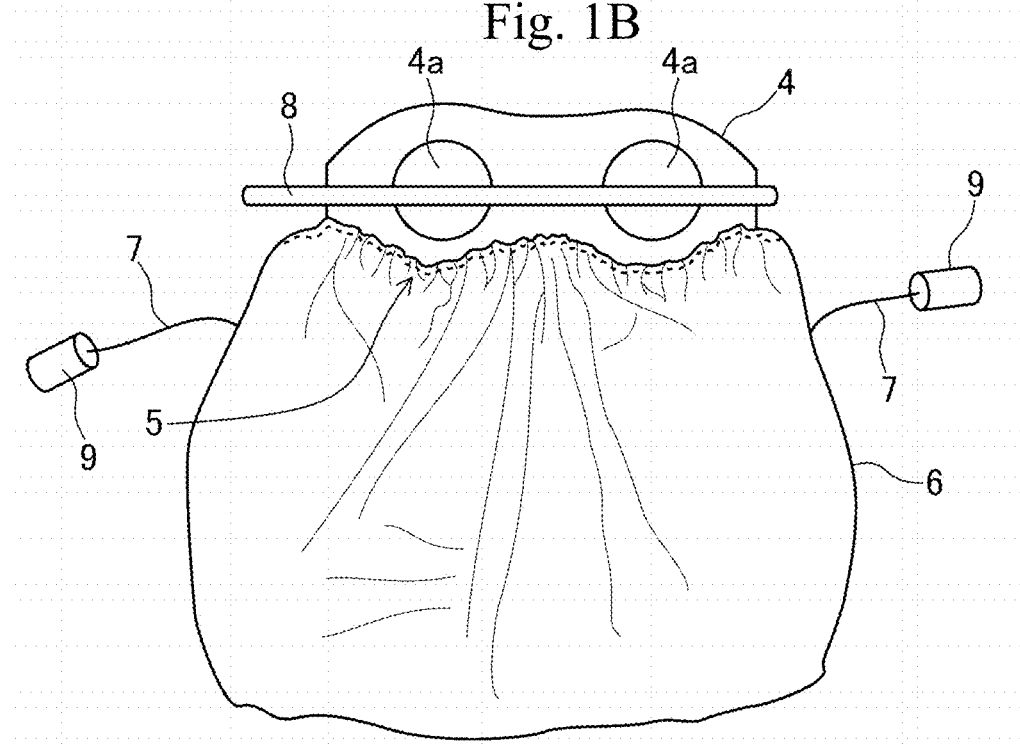
FIG. 1B is a rear view.
Figure 2:
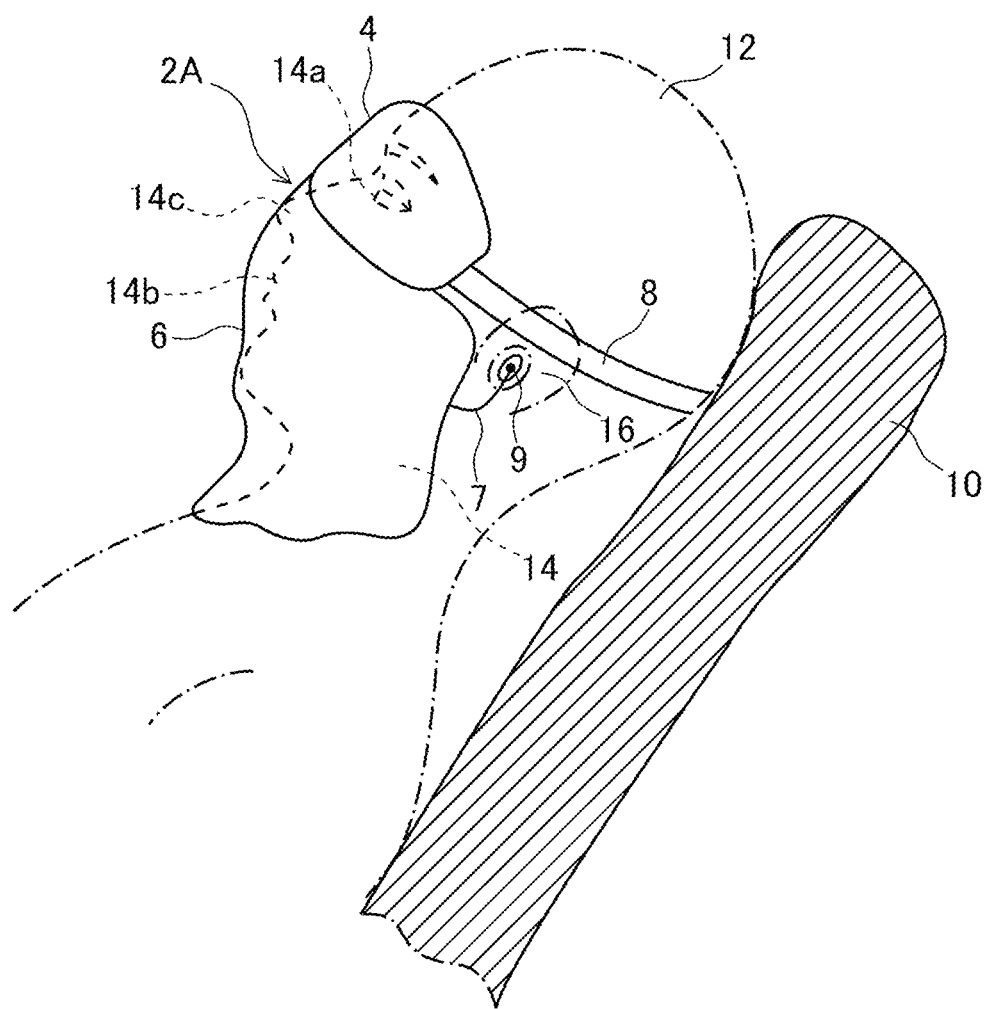
FIG. 2 A side view showing the usage state of the etiquette mask shown in FIG. 1.

Refer to FIGS. 1 and 2 for the explanation of the first embodiment. FIG. 1A is a front view of an etiquette mask 2A according to the first embodiment of the present invention, and FIG. 1B is a rear view thereof. The etiquette mask 2A comprises an upper mask part 4 covering the eye area 14a (eyes and its surrounding area) of the face 14, a lower mask part 6 attached to the upper mask part 4 and covering the area of the face below the eye area, a rubber band 8 provided on the upper mask part 4 as a mounting part to prevent the etiquette mask 2A from falling off the face, and earplugs 9 integrally attached to both sides of the upper end of the lower mask part 6 via flexible strings 7.

The upper mask part 4 is formed of a light-shielding material having flexibility, such as synthetic sponge, and as shown in FIG. 1B, a circular recess 4a is formed in the part corresponding to the eye area on the backside, to prevent it from hitting the eyes. Both ends of the rubber band 8 are respectively sewn onto both sides of the backside of the upper mask part 4, and the reference numeral 4b in FIG. 1A indicates the sewn part of the rubber band 8. The lower mask part 6 has an area sufficient to cover well below the eye area on the front surface of the face, and is formed of a soft and pleasant-feeling fabric, such as silk cloth, which can deform according to changes in facial contours. The lower mask part 6 is attached to the upper mask part 4 by sewing its upper side (the side shown as an arrow Z1) in the vertical direction (the direction shown as arrow Z) of the face to the lower end of the backside of the upper mask part 4. Also, the lower mask part 6 has a width larger than the width w of the upper mask part 4 and is closely sewn so as to form pleats. That is, a gather 5 is applied to a part (upper side). The periphery of the lower mask part 6, except for the upper side, is a free edge, and when the etiquette mask 2A is lifted, a plurality of wrinkles (folds, including the concept of drapes) 6a are randomly formed by the etiquette mask being drooped.

FIG. 2 shows the usage state of the etiquette mask 2A, which is an example of a situation where one is napping in a reclined state by leaning against the backrest 10 in train interiors, such as the Shinkansen, or inside an airplane. When you wear the etiquette mask 2A to cover the eye area 14a by fitting the rubber band 8 around the head 12, the soft and pleasant-feeling silk fabric of the lower mask part 6 deforms according to the deformation of the contours of the face 14 and covers a lower side below a part of eyes 14a on the face 14 in a drooping state due to its own weight.

This prevents the opening of the mouth 14b from being seen by others (other passengers) if it is unintentionally opened during a nap, thus avoiding any embarrassment. Also, since the lower mask part 6 fits on the surface of the face 14 by its own weight due to the softness of its fabric, it suppresses the concern of virus spread from the mouth 14b or nose 14c in situations where coronavirus countermeasures are being called for, contributing to compliance with social etiquette (consideration for those around). Since the lower mask part 6 itself simply covers the face 14 due to its own weight without having any attachment parts like rubber strings for the face 14, there is no oppressive feeling or difficulty of breathing like those caused by the elastic force of regular mask's rubber or the tightening force of strings, and there is less friction on the surface of the face 14, which can cause skin roughness. Especially in this embodiment, since gathers 5 are applied to the upper side of the lower mask part 6, even though the soft and pleasant-feeling fabric, the existence of the wrinkles 6a allows easy formation of a gap protruding outward from the face 14 at the part corresponding to the mouth 14b or nose 14c, thus having an advantage of being able to further reduce the difficulty of breathing. Moreover, by inserting earplugs 9 into the ear holes 16, surrounding noise can be blocked, thereby improving restfulness. Since the earplugs 9 are integrally attached to the lower mask part 6 with a string 7, they won't be forgotten, and there's no need to worry about their location even when not in use.

The material for the lower mask part 6 is not limited to soft fabric such as silk, and a general cloth may be adopted within a range of being able to prevent visibility from the outside. As a soft fabric with a nice touch, in addition to silk, velvet (velour), velour or the like can be adopted. These have an excellent sophisticated feeling, and there is no discomfort even when used in extraordinary places such as inside an airplane. Since the upper mask part 4 and the lower mask part 6 are integrated, there is no sense of heavy equipment, comparing with when wearing an eye mask and a regular mask at the same time, and the material, shape, and color tone of the lower mask part 6 can be added. Rather, it is possible to improve the fashionability. There is also no worry of forgetting either one.

Second Embodiment

Figure 3:
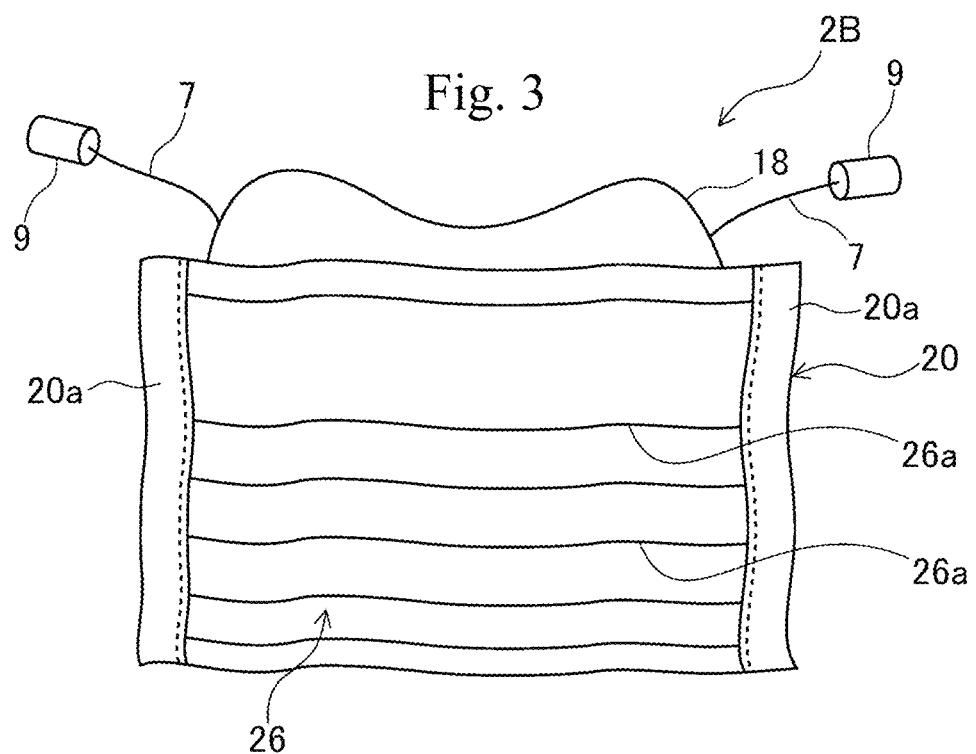
FIG. 3 A front view showing an etiquette mask according to the second embodiment.
Figure 4:
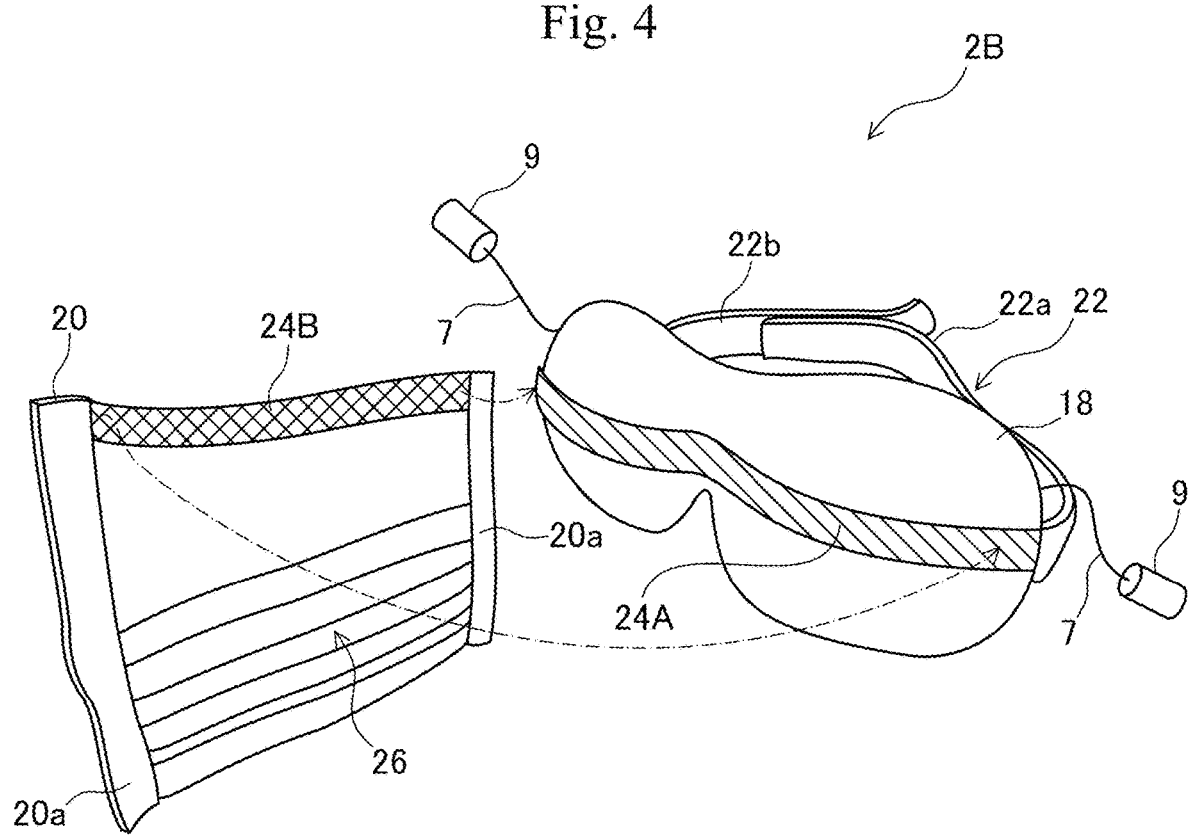
FIG. 4 An exploded perspective view of the etiquette mask shown in FIG. 2.
Figure 5:
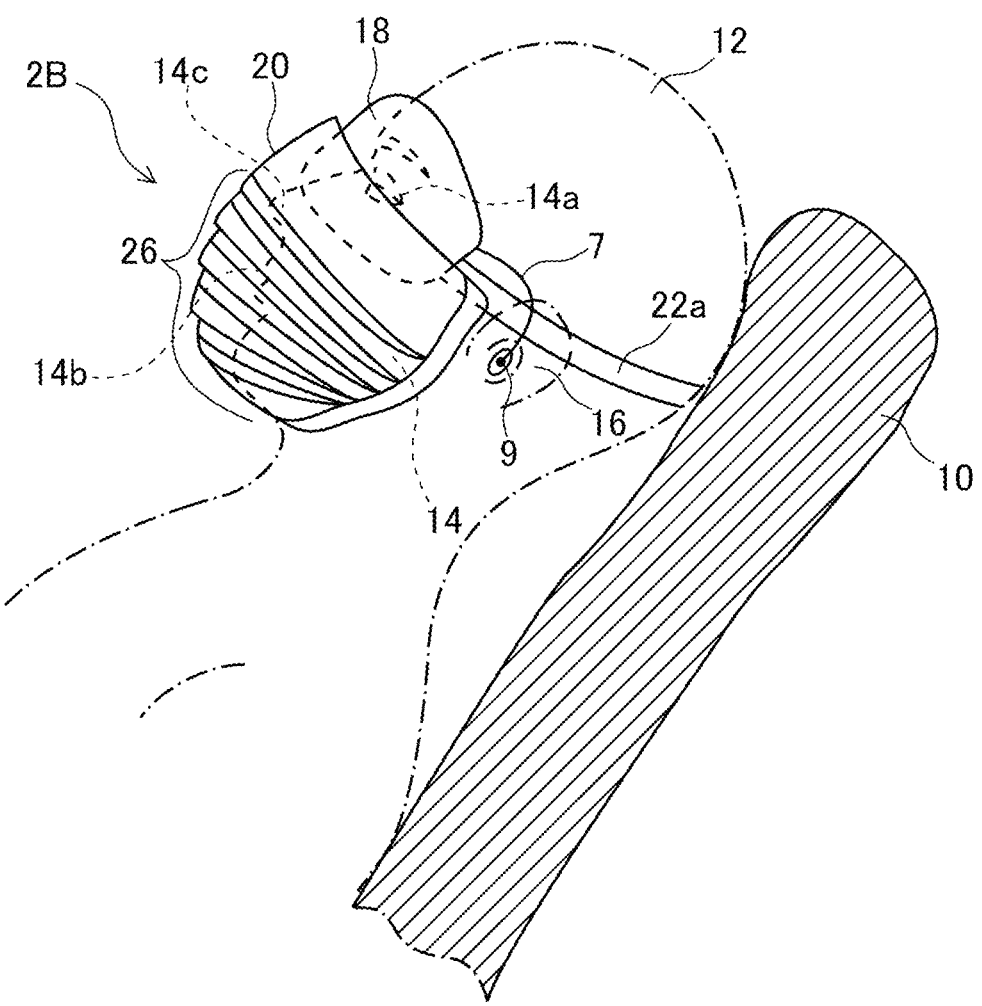
FIG. 5 A side view showing the usage state of the etiquette mask shown in FIG. 2.

Refer to FIGS. 3 to 5 for an explanation of the second embodiment. Note that the same parts as the first embodiment are indicated by the same reference numerals, and the duplicate description of their configuration and function will be omitted as appropriate (the same applies to other embodiments below).

FIG. 3 is a front view of an etiquette mask 2B according to this embodiment. The etiquette mask 2B comprises a thin upper mask part 18 made of a flexible synthetic resin, a lower mask part 20 that can be detachably attached to the surface side of the upper mask part 18 at the upper end portion thereof, a rubber band 22 (see FIG. 4) provided on the upper mask part 18 as a wearing portion to prevent the etiquette mask 2B from falling off the face 14, and earplugs 9 integrally attached to each both sides of the upper end part of the upper mask part 18 via flexible strings 7. A recess protruding outward from the face 14 is formed in the part corresponding to the eyes 14a of the upper mask part 18. The lower mask part 20 is formed in a rectangular shape with a normal cloth, the periphery is folded twice or more and sewn, and the rigidity (shape retention) is higher than that of a single layer. In particular, both vertical edges 20a are folded three times or more to increase rigidity and provide a frame function in the vertical direction of the face 14.

As shown in FIG. 4, a tape-shaped (band-shaped) planar fastener 24A is fixed to the entire width direction on the surface side of the upper mask part 18, and a tape-shaped planar fastener 24B that engages with the planar fastener 24A is fixed to the backside of the upper part of the lower mask part 20. As a result, the lower mask part 20 can be detachably attached to the upper mask part 18. The rubber band 22 consists of two bands 22a, 22b, one end of each is fixed to the upper mask part 18, and the free ends of each band 22a, 22b can be fixed at any position to each other by a not shown planar fastener. By shifting the fixed position between the free ends, the tightening force of the rubber band 22 on the head 12 can be adjusted.

The lower half of the lower mask part 20 has a bellows-fold configuration 26 that presents a curved shape that protrudes outward from the face 14 by pulling in the vertical direction (downward direction, that is, the Z2 direction in FIG. 1) of the face 14. The bellows-fold configuration 26, which can also be called a horizontal pleat type, has multiple (five in this case) fold lines 26a, and the lower mask part 20 itself is flat and rectangular when not being pulled.

FIG. 5 shows the usage state of the etiquette mask 2B. When the rubber band 22 is fitted to the head 12 and the etiquette mask 2B is worn to cover the area of the eyes 14a, and the lower end of the lower mask part 20 is pinched with fingers and pulled downward, like a pleated-type mask, the bellows-fold configuration 26 expands and takes on a curved shape protruding outward from the face 14. By combining the stiffness provided by folding creases 26a with the stiffness provided by overlap-sewing of the periphery, to the lower part 20 is maintained in a curved shape that forms a space (gap) at the areas corresponding to the nose 14c and mouth 14b. As the lower mask part 20 is only supported at the upper end thereof by the upper mask part 18, there is no sense of oppression or difficulty of breathing through the elastic force of the rubber or the tightening force of the strings. Unlike soft fabrics such as silk, a wide space is reliably formed around the mouth 14b and nose 14c, thus reducing the feeling of oppression and difficulty of breathing even further and making it possible to breathe easier. After use, the expanded bellows-fold configuration 26 can be folded back to its original flat shape.

In this embodiment, since the lower mask part 20 is detachably provided on the upper mask part 18, it has the advantage of being easy to replace in case of getting dirty or according to pattern or color preference. In addition, only the lower mask part 20 can be removed and washed, and further, due to its flat shape, multiple pieces can be stacked (flat stacked) for compact and easy storage.

Third Embodiment

Figure 6A:
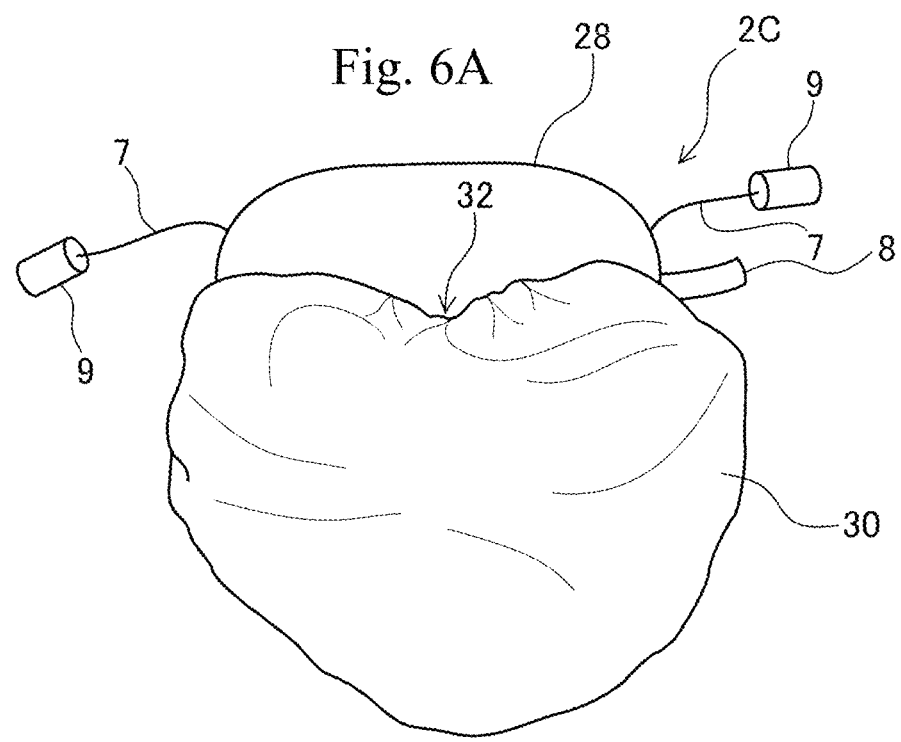
FIG. 6A is a front view.
Figure 6B:
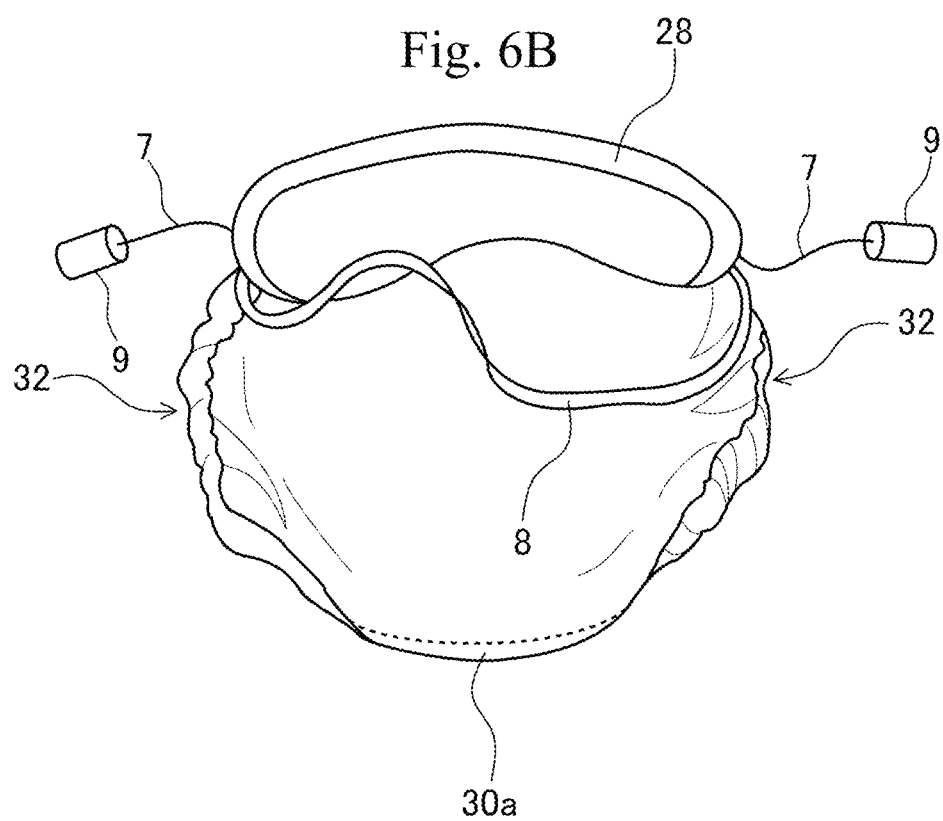
FIG. 6B is a rear view.

Refer to FIG. 6 for an explanation of the third embodiment. FIG. 6A is a front view of an etiquette mask 2C according to this embodiment, and FIG. 6B is a rear view. The etiquette mask 2C includes an upper mask part 28 formed of a synthetic sponge or the like, a lower mask part 30 attached to the upper mask part 28 and covering the lower side of the face 14 from the area of the eyes 14a, a rubber band 8 provided on the upper mask part 28 as a mounting part to prevent the etiquette mask 2C from falling off the face 14, and earplugs 9 integrally attached to both ends of the upper mask part 20 via strings 7.

The lower mask part 30 is attached by sewing its upper side to the lower end of the surface side of the upper mask part 20. The central part of the upper side of the lower mask part 30, as well as both sides of other parts excluding the upper side, have gathers 32. That is, gathers 32 are provided on at least a part of the periphery of the lower mask part 30, so that in the state before use, the lower mask part 30 has a curved shape protruding outward from the face 14. Although the lower mask part 30 is formed of a thin fabric, it has shape retention, due to the gathers 32, for maintaining a curved shape protruding outward from the face 14. To make it easier to enter into a underside of the jaw, no gathers 32 are provided on the lower side 30a of the lower mask part 30. Therefore, without the need to pull and expand the bellows-fold configuration 26 as shown in the second embodiment, when wearing the etiquette mask 2C, the face 14 is covered with the lower mask part 30 in an expanded state, thus reducing feelings of oppression and difficulty of breathing, and making breathing easier.

Fourth Embodiment

Figure 7A:
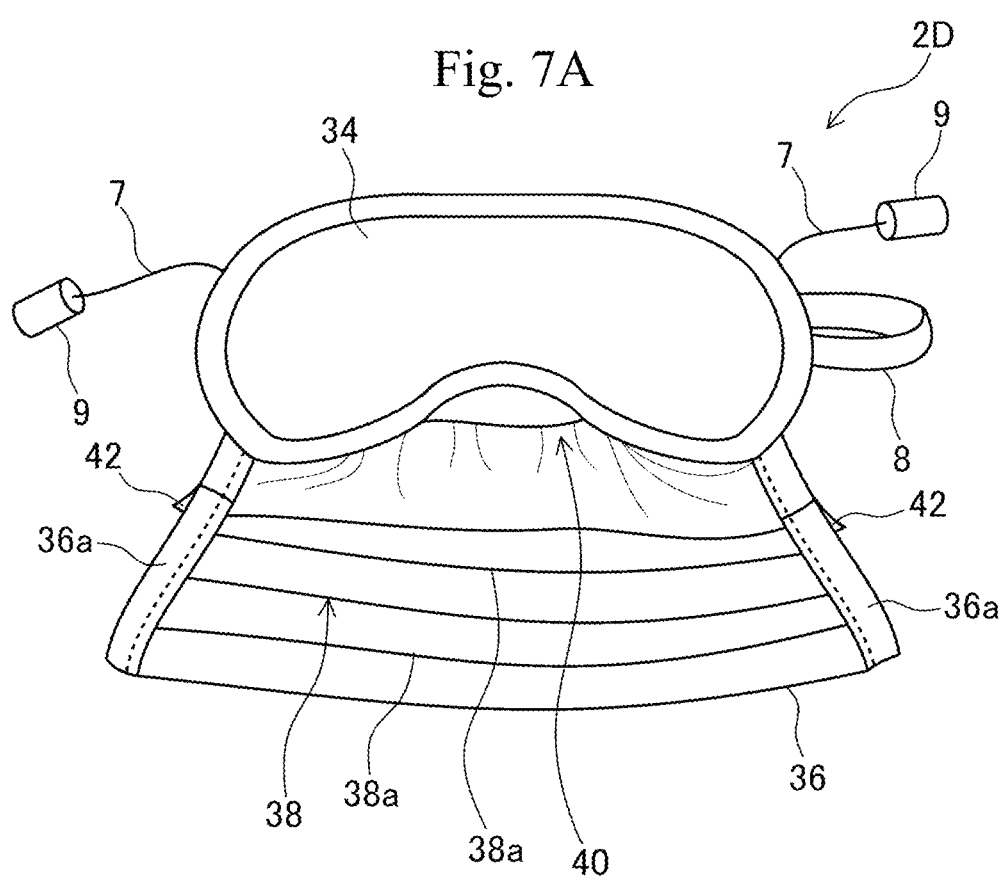
FIG. 7A is a front view.
Figure 7B:
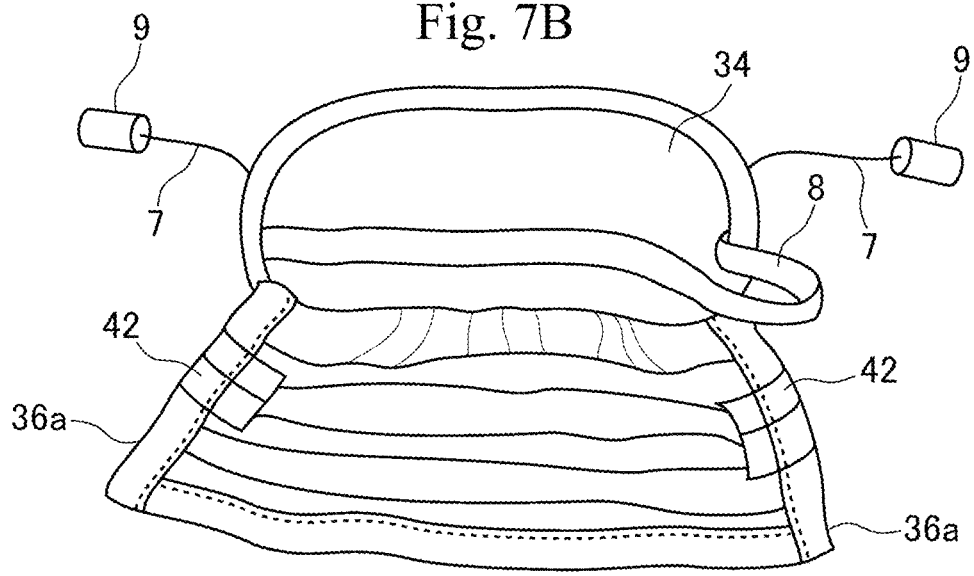
FIG. 7B is a rear view.

Refer to FIG. 7 for an explanation of the fourth embodiment. FIG. 7A is a front view of an etiquette mask 2D according to this embodiment, and FIG. 7B is a rear view. The etiquette mask 2D includes a flexible upper mask part 34 formed of synthetic fibers, a lower mask part 36 attached to the upper mask part 34 and covering the lower side of the face 14 from the area of the eyes 14a, a rubber band 8 provided on the upper mask part 34 as a mounting part to prevent the etiquette mask 2D from falling off the face 14, and earplugs 9 integrally attached to both sides of the upper end of the upper mask part 34 via flexible strings 7.

The upper mask section 34 has a configuration that outlines the periphery of a cushioning body made of multiple layers. Although there are no recess in the portion corresponding to the eye areas 14a, its softness makes it possible to attain soft touch. The lower mask section 36 has a bellows-fold configuration 38 similar to the lower mask section 20 in the second embodiment. The upper side of the lower mask section 36 is sewn to the lower end of the upper mask section 34 by providing gathers 40 and gathers 42 which are taken in once are also provided on vertical edges 36a on both sides of the mask. This makes it easier to form a curved shape that covers the face 14. In FIG. 7, the reference numeral 38a indicates the fold of the bellows-fold configuration 38.

Fifth Embodiment

Figure 8A:
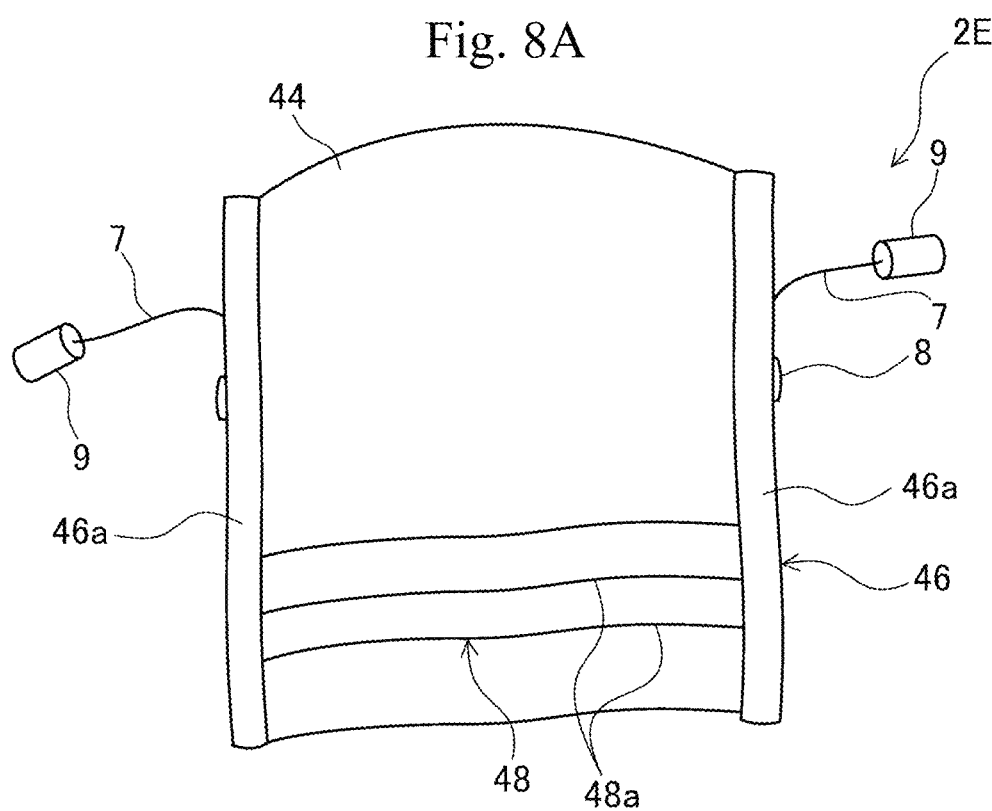
FIG. 8A is a front view.
Figure 8B:
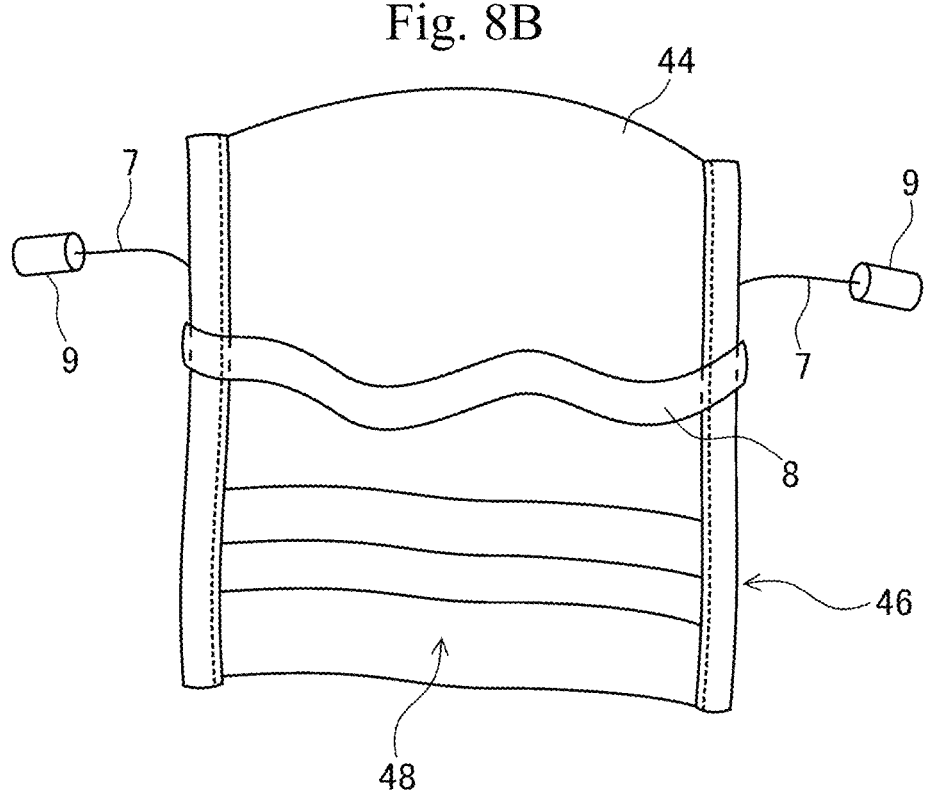
FIG. 8B is a rear view.
Figure 9:
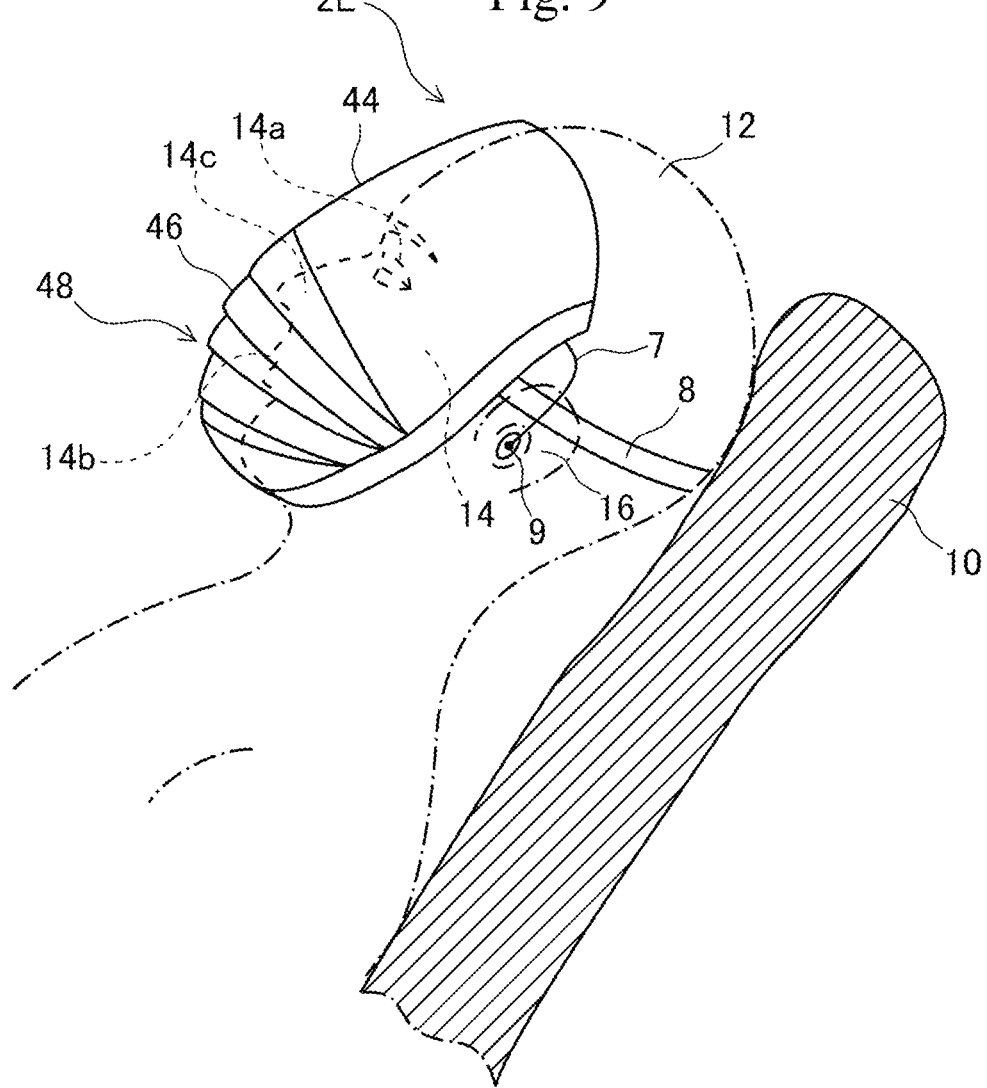
FIG. 9 A side view showing the usage state of the etiquette mask shown in FIG. 8.

The Fifth Embodiment will be described with reference to FIGS. 8 and 9. FIG. 8A is a front view of the etiquette mask 2E according to this embodiment, and FIG. 8B is a rear view. The etiquette mask 2E includes a fabric upper mask section 44 that covers the forehead and eye areas on the face, a lower mask section 46 formed in a series with the same material as the upper mask section 44 and covering the lower side of the eye areas 14a on the face 14, a rubber band 8 provided on the upper mask section 44 as a mounting part that prevents the etiquette mask 2E from falling off from the face 14, and ear plugs 9 attached integrally through flexible cords 7 on both sides of the upper end of the upper mask section 44.

The upper mask section 44 has a longer vertical dimension, comparing with the upper masks in Embodiments 1 to 4. Therefore, the upper mask section 44 can cover not only the eye areas 14a (around the eyes) on the face 14, but also almost the entire forehead (up to the hairline). The lower mask section 46 is formed with a bellows-fold configuration 48 having multiple folds 48a. FIG. 9 shows the usage state of the etiquette mask 2E. In this embodiment, the upper mask section 44 and the lower mask section 46 can be formed in series (integrated) by folding or pleating a single piece of cloth, thus achieving improved manufacturing efficiency and cost reduction. Also, when not in use, it becomes flat, providing compact and easy storage and space-saving during distribution process.

Sixth Embodiment

Sixth Embodiment will be described with reference to FIGS. 10 and 11. In each of the above embodiments, the eye areas 14a are completely shielded by the upper mask section 4 and the like, and the mouth area 14b is substantially sealed by the lower mask section 6 and the like. There may be times when one wants to see the surroundings without removing the etiquette mask 2A, and times when one wants to breathe fresh air directly into the mouth 14b and/or nose 14c in case that it becomes difficult to breathe. This embodiment responds to such requests.

Figure 10A:
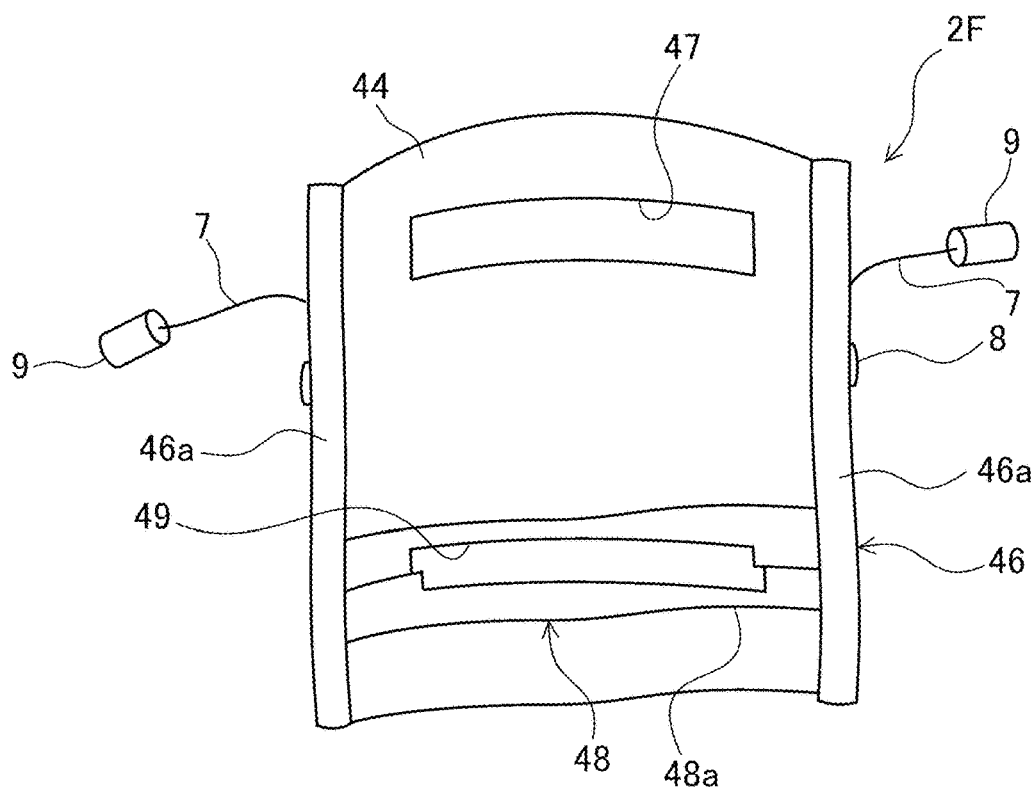
FIG. 10 An perspective view showing an etiquette mask according to the sixth embodiment.
Figure 10B:
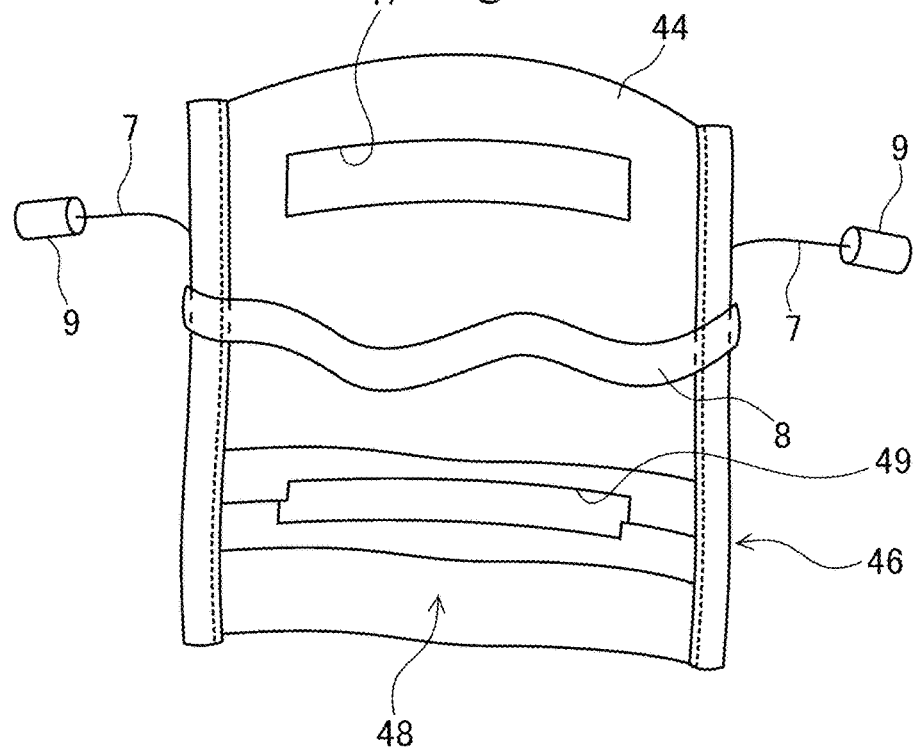

FIG. 10A is a front view of the etiquette mask 2F according to this embodiment, and FIG. 10B is a rear view. In this embodiment, the etiquette mask 2F, in addition to the etiquette mask 2E of the fifth embodiment, has a slit-shaped opening 47 at a position corresponding to the eye areas 14a on the upper mask section 44, and a slit-shaped opening 49 at a position corresponding to the mouth 14b and its surroundings on the lower mask section 46. The rest of the structure is the same as the etiquette mask 2E of the fifth embodiment.

Figure 11:
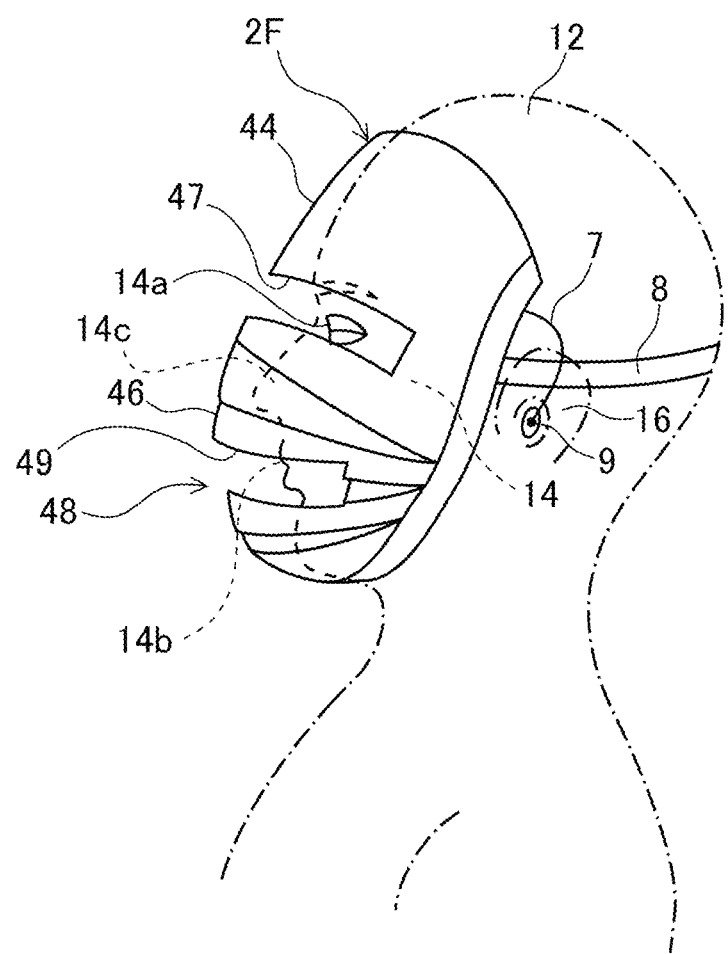
FIG. 11 A side view showing the usage state of the etiquette mask shown in FIG. 10.

FIG. 11 shows the usage state of the etiquette mask 2F. The etiquette mask 2F of this embodiment can also be used to prevent sunburn on the face by wearing this etiquette mask when doing agricultural work, etc. In that case, because an opening 47 is provided on the upper mask section 44, the opening 47 can ensure visibility, so you can do agricultural work, etc. while wearing the etiquette mask 2F. Also, because an opening 49 is provided in the lower mask section 46, during breaks in agricultural work, etc., you can drink or eat light meals while wearing the etiquette mask 2F. Also, the effect of making it easier for the wearer's voice to be heard outside through the opening 49 can be obtained.

Seventh Embodiment

Figure 12:
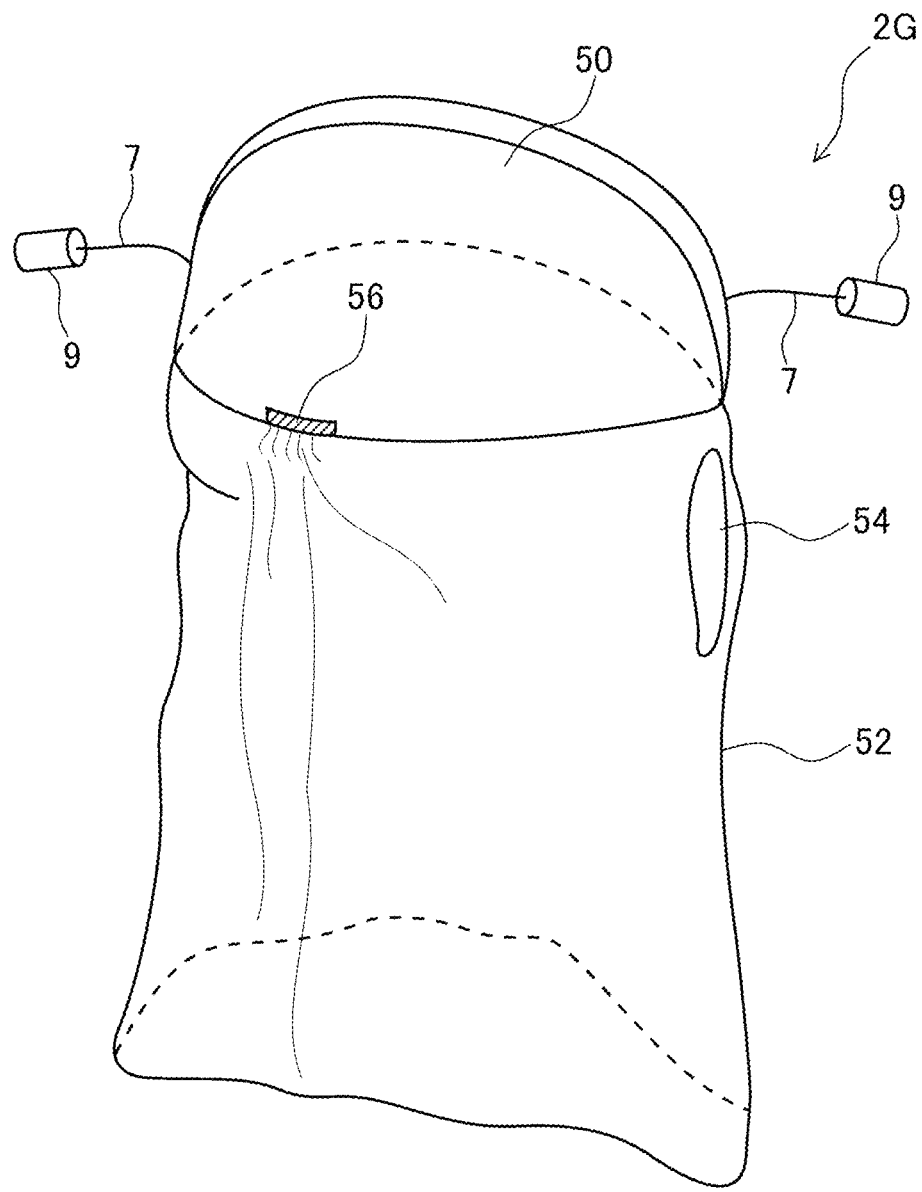
FIG. 12 An perspective view showing the etiquette mask according to the seventh embodiment.
Figure 13:
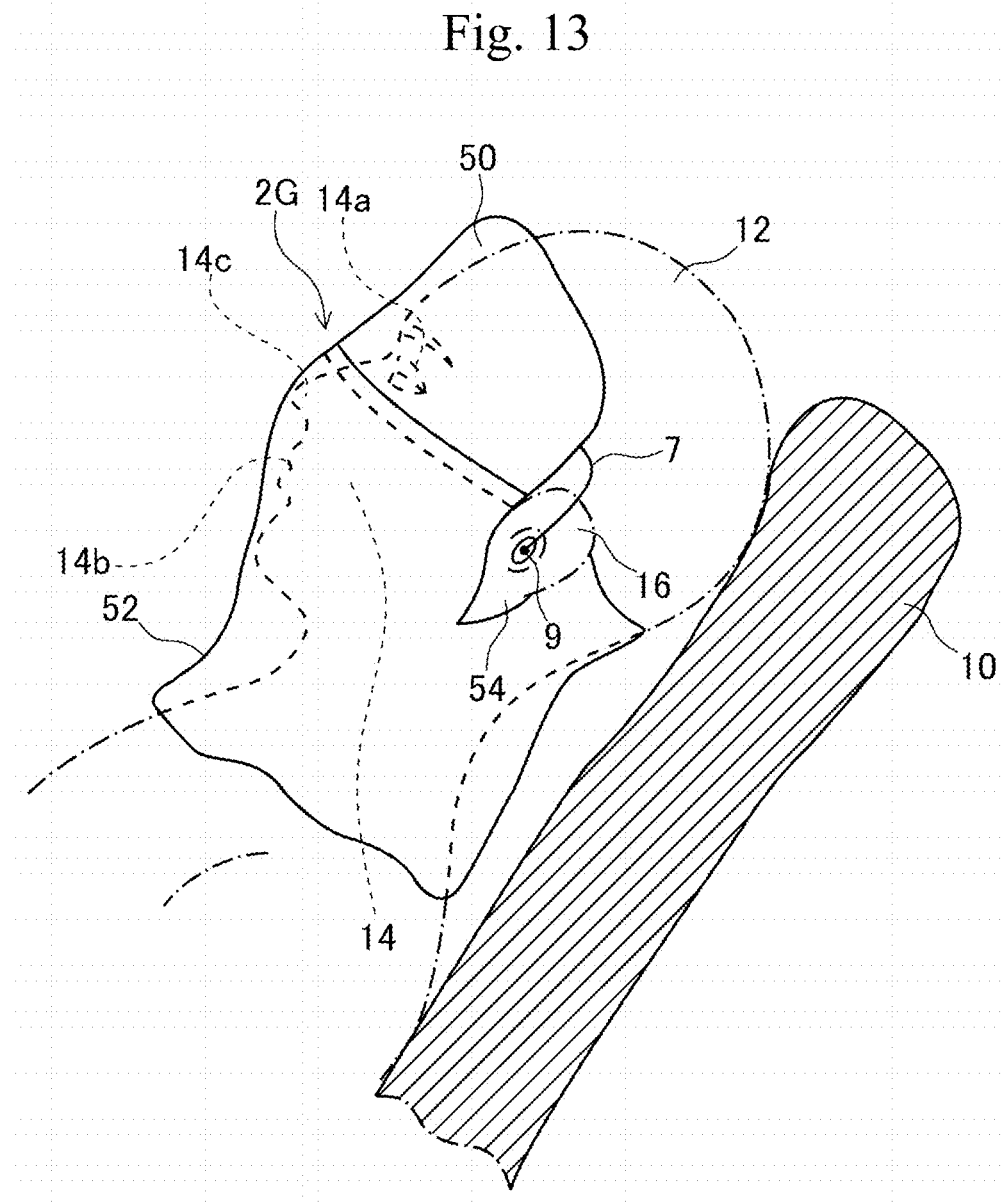
FIG. 13 A side view showing the usage state of the etiquette mask shown in FIG. 12.

Seventh Embodiment will be described with reference to FIGS. 12 and 13. In each of the above embodiments, the lower mask part is configured to cover only the front side of the face 14, but this embodiment is characterized by a configuration that covers the entire neck area including the side of the face 14. FIG. 12 is a perspective view of the etiquette mask 2G according to this embodiment. The etiquette mask 2G includes an upper mask part 50 made of a synthetic sponge, a cylindrical lower mask part 52 that is detachably attached to the lower end of the surface side of the upper mask part 50 at an upper end side thereof, holes 54 for hanging the mask to the ears which are opened on both sides of the lower mask part 52 as a mounting part, and ear plugs 9 attached integrally through flexible cords 7 on both sides of the upper end of the upper mask part 50.

The upper mask part 50 is longer in the vertical dimension, comparing with those of the upper masks of Embodiments 1 to 4. Therefore, the upper mask part 50 can cover not only the eye areas 14a (around the eyes) on the face 14, but also almost the entire forehead (up to the hairline). Also, the lower mask part 52 is made of a fabric which is good in touch, such as silk, similar to the first embodiment, and is detachably attached at least at three positions on the center and both sides of the surface side, by using hook-and-loop fasteners 56 and unillustrated hook-and-loop fasteners engaged with them. FIG. 13 shows the usage state of the etiquette mask 2G. When wearing the etiquette mask 2G on the face, the head 12 is inserted into the lower mask part 52, and the ears 16 are inserted into the holes 54 respectively to hook the etiquette mask on the ears. Like the above embodiments, Such a configuration may be adapted that a rubber band or the like is provided on the upper mask part 50 as a mounting part, but by providing the holes 54 for hanging the mask to ears, a natural wearing feeling without a sense of tightening can be obtained. Also, since the lower mask part 52 is a cylindrical shape to cover the face and neck, it has the advantage of preventing the neck from getting cold during naps or sleep in winter or under air conditioning in summer.

Also, the etiquette mask 2G of this embodiment allows the lower mask part 52 to be separated from (removed from) the upper mask part 50, and the lower mask part 52 can be used alone. In this case, the lower mask part 52 can be used outdoors for a sunshade or cold protection. That is, by wearing only the lower mask part 52 on the face and around the neck during agricultural work, etc., it can be used as clothing to prevent sunburn on the face and neck, or as clothing for cold protection in winter. Also, when using the lower mask part 52 alone, it can be used as clothing for fashion when going out, like a scarf or a neck warmer.

Eighth Embodiment

Eighth Embodiment will be described with reference to FIGS. 14 and 15. In the previous embodiment 6, a configuration was adopted in which a slit-shaped opening 49 was provided in the lower mask part 46, but the disadvantage caused by maintaining the open state as is cannot be denied. That is, although the facial expression of the face 14 cannot be seen from the outside, it is possible to grasp the opening state of the mouth 14b from the opening 49, and depending on the place and situation where it is worn, this may give discomfort to the surroundings. This is especially the case under infection control measures. This embodiment is made to solve such problems and its purpose is to be able to directly inhale outside air when feeling suffocated, and also to be able to arbitrarily return to a state of etiquette observance that does not give discomfort to the surroundings.

Figure 14A:
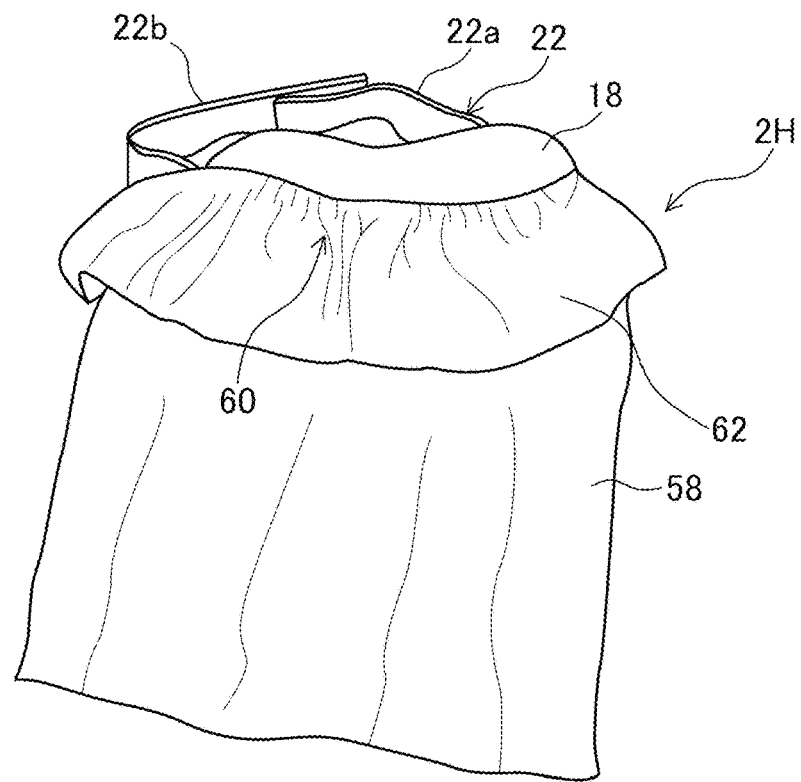
FIG. 14A is a front view.

As shown in FIG. 14A, the etiquette mask 2H according to this embodiment includes a thin flexible upper mask part 18 made of synthetic resin material or cloth material, a lower mask part 58 attached to the surface side of the upper mask part 18 at an upper end side thereof by sewing or joining hook-and-loop fasteners together, a cover 62 sewn to the upper end of the lower mask part 58 at a upper end side thereof while applying gathers 60 to the cover, and a rubber band 22 provided on the upper mask part 18 as a mounting part to prevent the etiquette mask 2H from falling off from the face 14. The lower mask part 58 and the cover 62 are formed of a soft fabric that deforms according to the changes in the irregularities of the face 14. In this embodiment and the following embodiments, ear plugs 9 are not provided, but ear plugs 9 can be provided as appropriate.

Figure 14B:
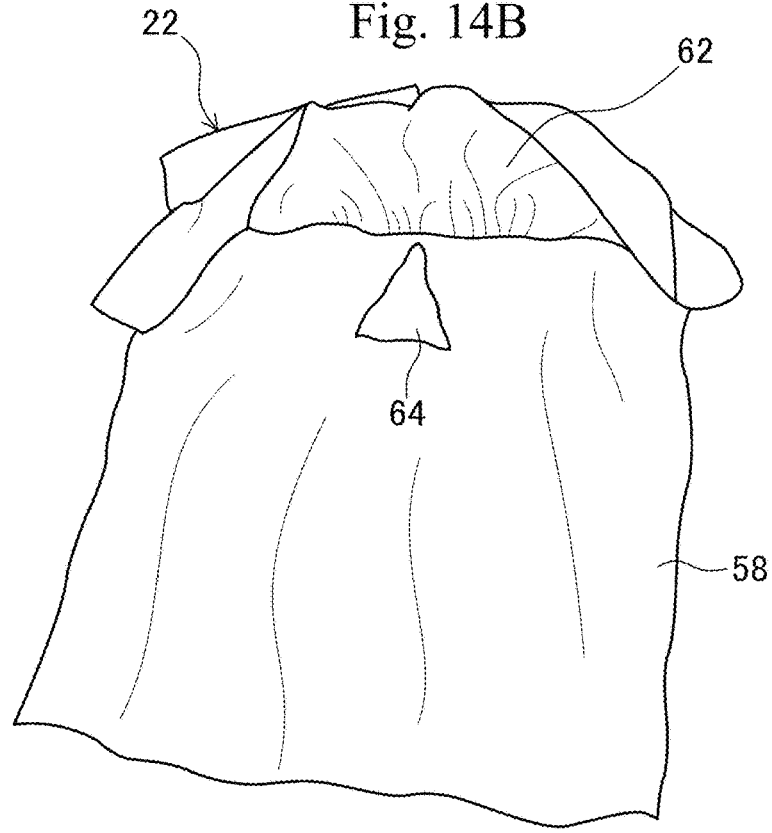
FIG. 14B is a front view showing the state with the covering cover rolled up.

FIG. 14B shows the state in which the cover 62 has been rolled upward in the vertical direction on the face 14. As clear from the figure, the lower mask part 58 includes an opening 64 of a size capable of exposing the nose 14c at a position corresponding to the nose part 14c on the face 14. When the cover 62 is lowered, as shown in FIG. 14A, the opening 64 is covered by the cover 62 and becomes invisible from the outside. That is, the cover 62 covers the opening 64 in a way that it can be opened and closed. In this embodiment, the cover 62 is made with frills for females, but for males, it can be made simple with a dark color, for instance, without frills.

Figure 15:
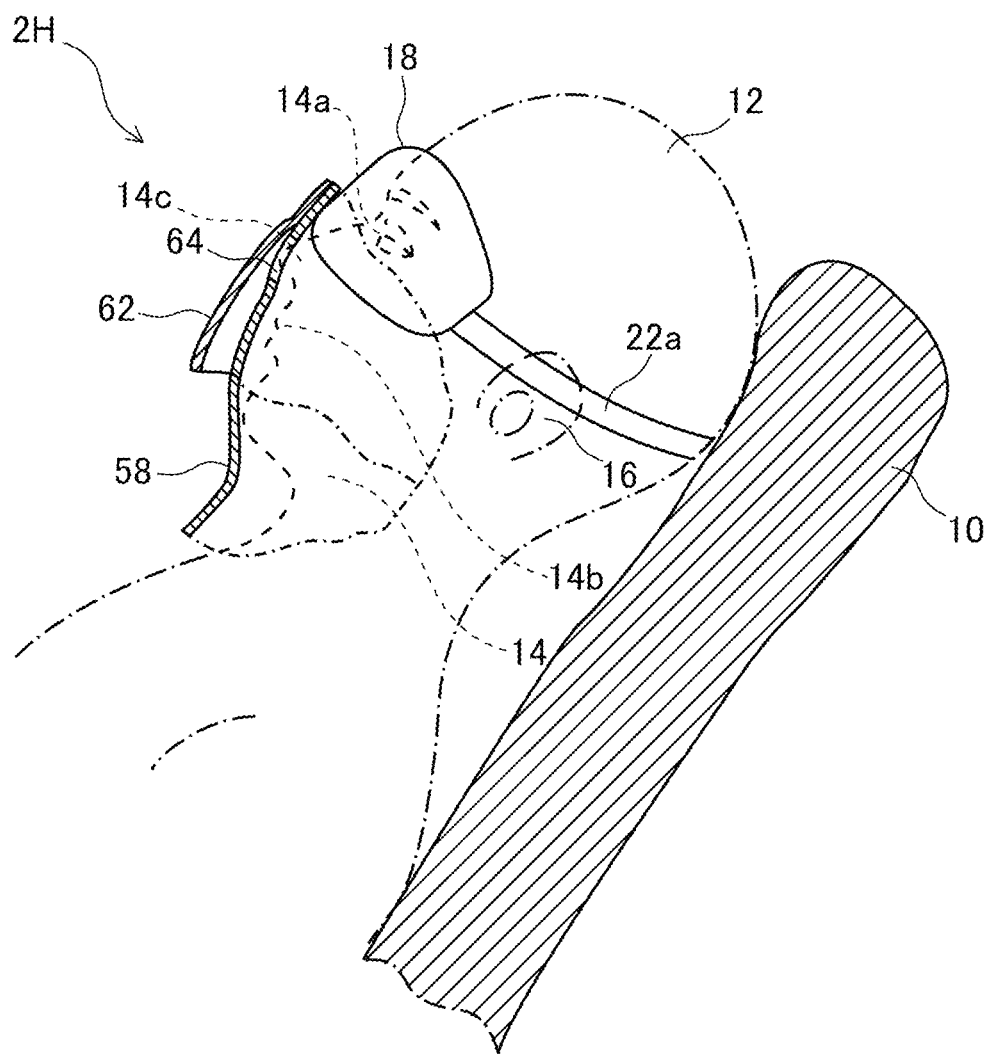
FIG. 15 A schematic cross-sectional view showing the usage state of the etiquette mask shown in FIG. 14.

FIG. 15 shows the usage state of the etiquette mask 2H. As shown in FIG. 15, the opening 64 is covered with the cover 62, and in the state where the cover 62 is lowered, it is almost the same as the state where no opening 64 is formed in the lower mask part 58. From this state, depending on the need of the user, for example, if the user feels suffocated and rolls up the cover 62, the opening 64 will be exposed to the outside, and they can directly inhale outside air through the nose 14c. Lowering the cover 62 will make the etiquette mask return to a state that does not give discomfort to the surroundings (the state of observing etiquette). In this way, a simple operation of raising and lowering the cover 62 can satisfy the user's desire to breathe outside air while observing etiquette. Compared with rolling up the entire lower mask part 58 to inhale outside air, any discomfort feeling is almost not brought to the surroundings, because the covering cover 64 is rolled up only partially and temporarily. The lower mask part 58 and the cover 62 are both made of thin cloth, but for easy understanding, the thickness in the cross section is exaggeratedly shown (the same exaggeration is applied to the figures in the other embodiments below).

If the cover 62 is too soft and falls down even when rolled up, it may be supported by hand while inhaling outside air, or a thin cloth with stiffness can be used to prevent it from falling down.

Ninth Embodiment

Figure 16:
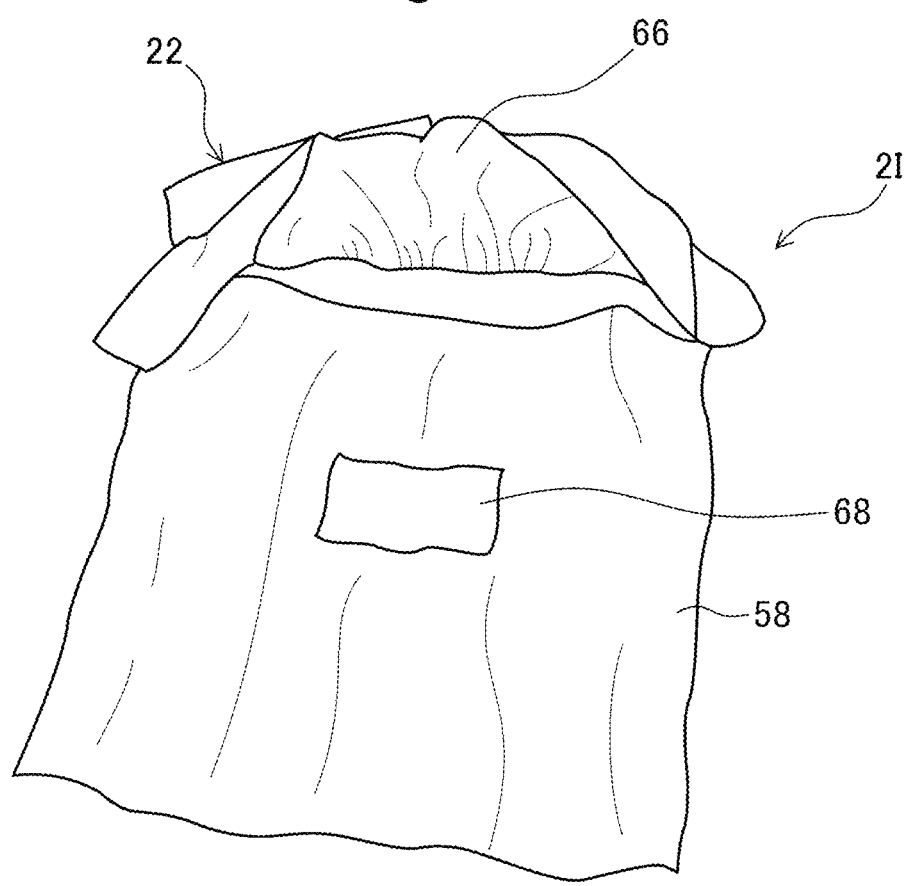
FIG. 16 A front view showing an etiquette mask according to the ninth embodiment, showing the state with the covering cover rolled up.

Ninth Embodiment will be described with reference to FIGS. 16 and 17. FIG. 16 shows the state where the cover 66 is rolled up in the vertical direction on the face 14. The etiquette mask 2I according to this embodiment includes an opening 68 at a position corresponding to the mouth 14b on the lower mask part 58. The configuration is basically the same as that in the eighth embodiment, except that the opening 68 is provided at a position corresponding to the mouth 14b, and as a result, the vertical length of the face 14 of the cover 66 is longer.

Figure 17:
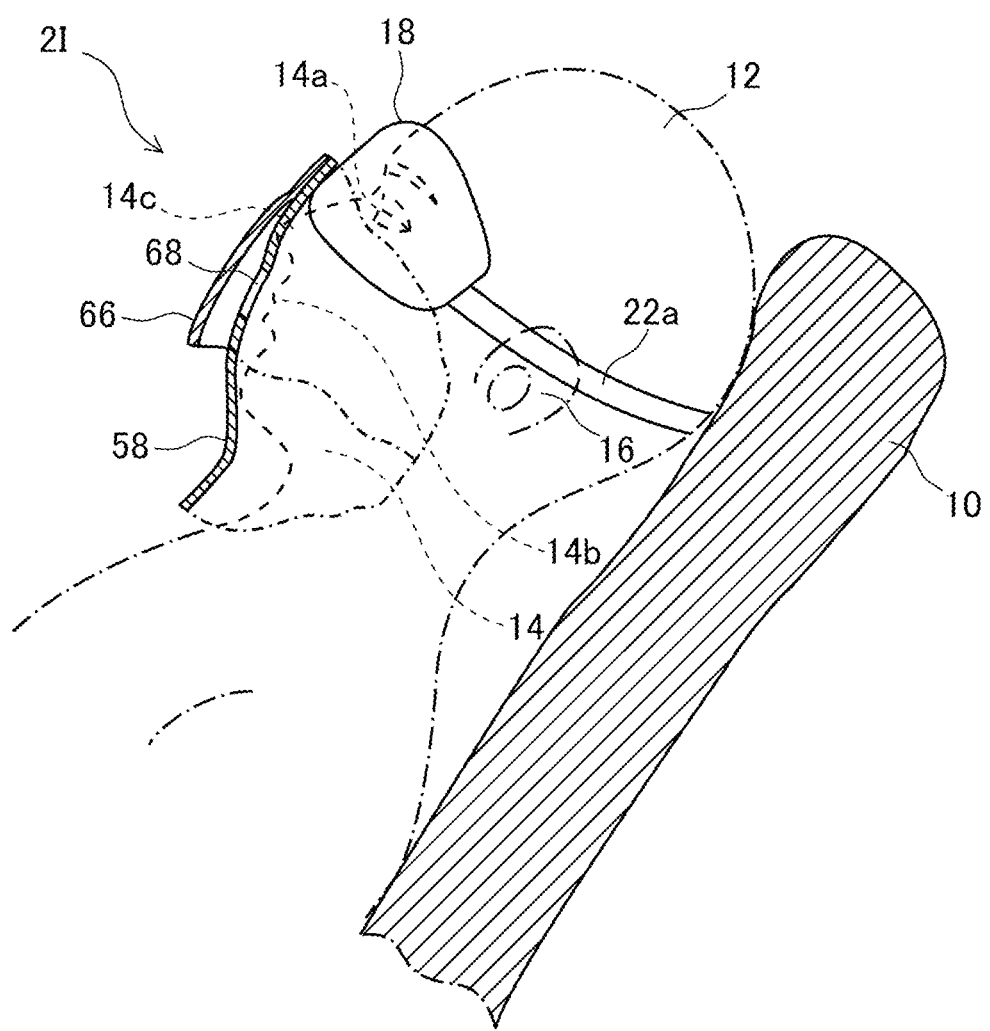
FIG. 17 A schematic cross-sectional view showing the usage state of the etiquette mask shown in FIG. 16.

FIG. 17 shows the usage state of the etiquette mask 2I. As shown in FIG. 17, the opening 68 is covered with the cover 66, and it is almost the same as the state where no opening 68 is formed in the lower mask part 58. From this state, if the user rolls up the cover 66 as needed, for example, if the user feels difficulty of breathing, the opening 68 will be exposed to the outside, and the user can directly inhale outside air through the mouth 14b. Lowering the cover 66 will return to a state that does not give discomfort to the surroundings (the state of observing etiquette).

Furthermore, aside from what is illustrated, the lower mask part 58 may be configured to include both an opening 64 corresponding to the nose area 14c and an opening 68 corresponding to the mouth area 14b, both of which can be opened and closed by the cover 66. In this case, both the mouth 14b and the nose 14c can inhale outside air at the same time.

Tenth Embodiment

Figure 18:
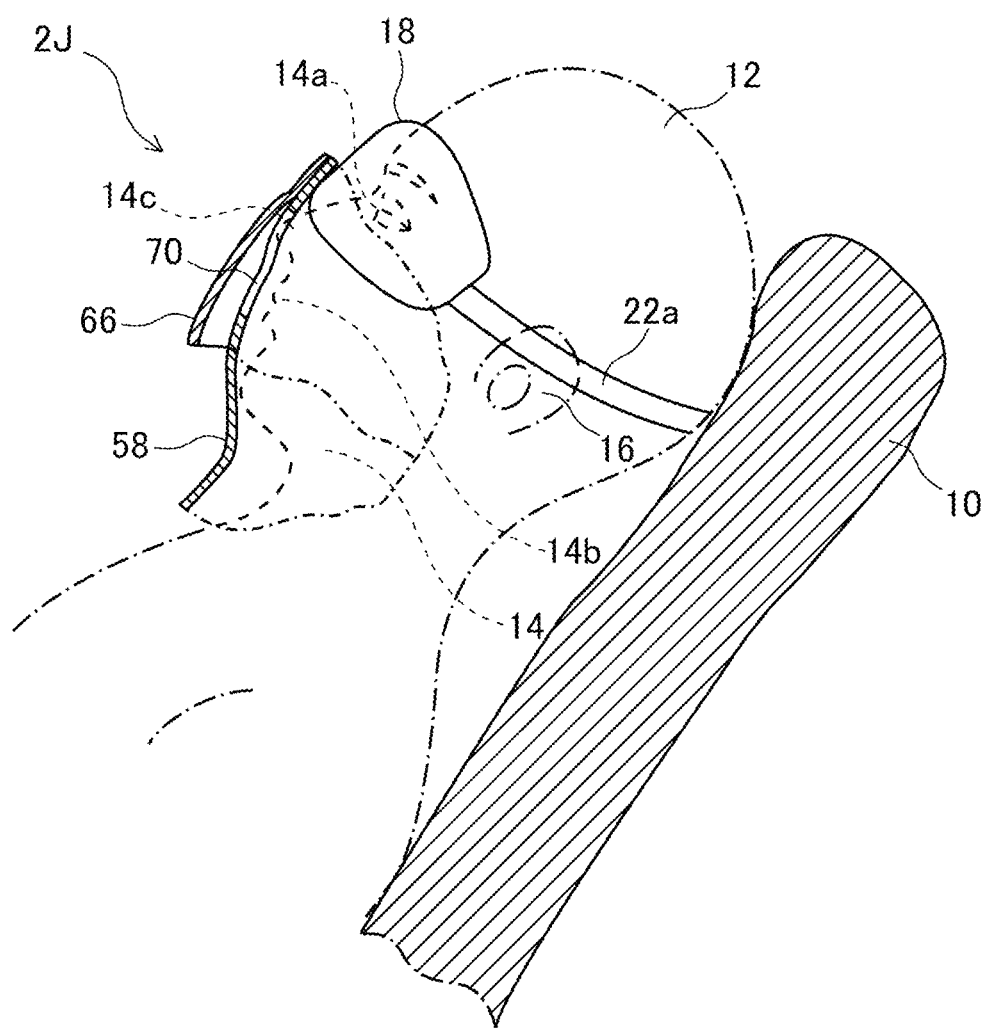
FIG. 18 A schematic cross-sectional view showing the usage state of an etiquette mask according to the tenth embodiment, in the state without rolling up the covering cover.

Refer to FIG. 18 to explain the tenth embodiment. In the etiquette mask 2J according to this embodiment, the lower mask part 58 includes a single opening 70 that serves both the opening 64 corresponding to the nose part 14c (refer to FIG. 15) and the opening 68 corresponding to the mouth part 14b (refer to FIG. 17). The opening 70 is covered by the cover 66, and when the cover 66 is rolled up, the opening 70 is exposed to the outside, and both the mouth 14b and the nose 14c can inhale outside air. This makes manufacturing easier than individually forming the opening 64 corresponding to the nose part 14c and the opening 60 corresponding to the mouth part 14b.

Eleventh Embodiment

Figure 19:
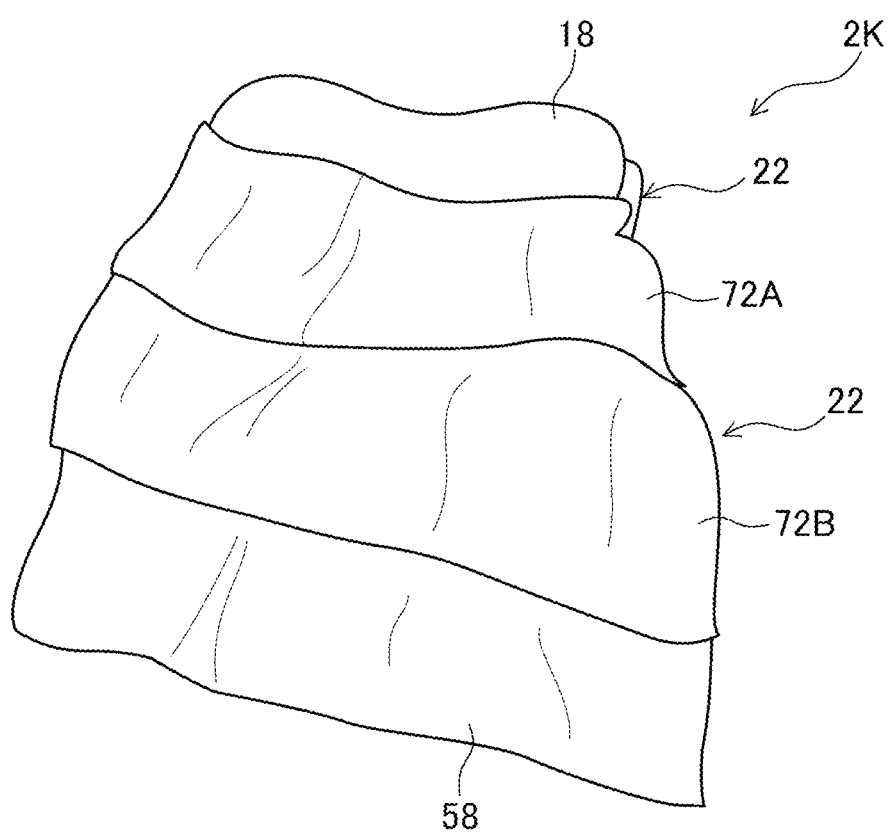
FIG. 19 A front view showing an etiquette mask according to the eleventh embodiment.
Figure 20A:
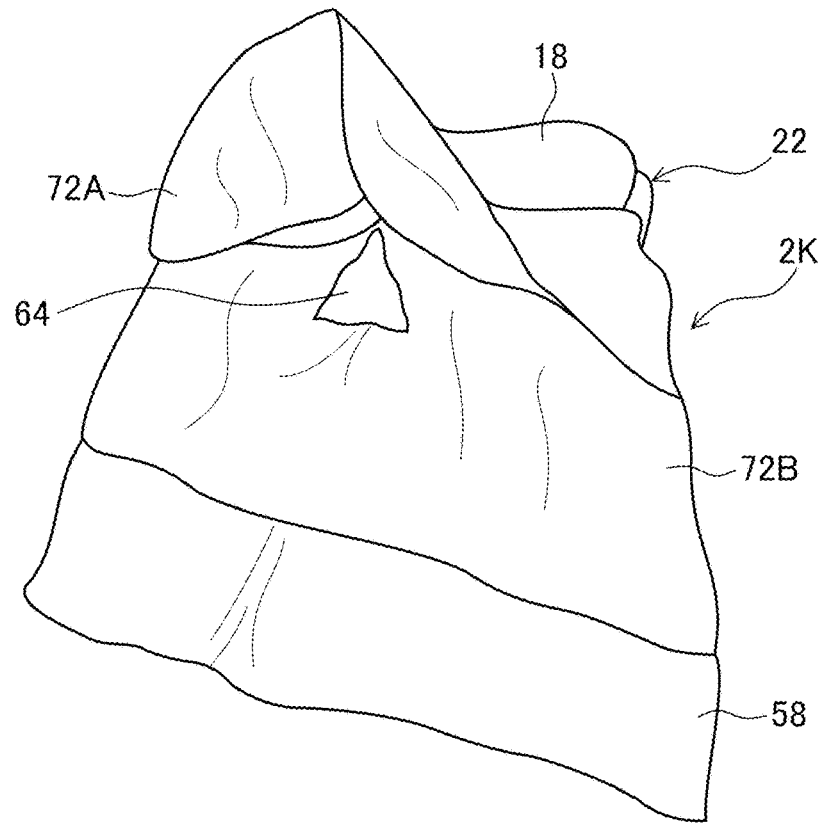
FIG. 20A shows the state with the upper cover rolled up.
Figure 20B:
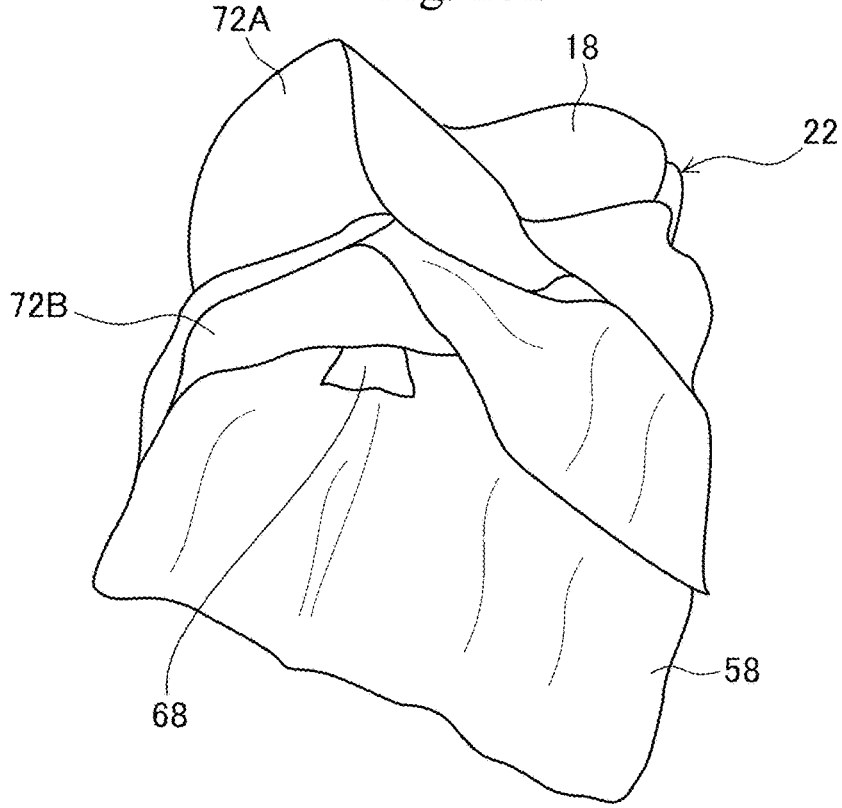
FIG. 20B shows the state with the lower cover rolled up.

Refer to FIGS. 19 to 22 to explain the eleventh embodiment. As shown in FIG. 19, the etiquette mask 2K according to this embodiment is characterized in that the cover 72 consists of an upper cover 72A covering the opening 64 corresponding to the nose part 14c and a lower cover 72B covering the opening 68 corresponding to the mouth part 14b. The lower cover 72B is longer in the vertical direction of the face 14 than the upper cover 72A and is arranged to overlap the lower surface of the upper cover 72A. FIG. 20A shows the state where the upper cover 72A is rolled up, and FIG. 20B shows the state where the lower cover 72B is further rolled up from that state. When the upper cover 72A is rolled up, the opening 64 corresponding to the nose part 14c is exposed to the outside, and when the lower cover 72B is rolled up, the opening 68 corresponding to the mouth part 14b is exposed to the outside and the opening 64 corresponding to the nose part 14c is exposed to the outside.

Figure 21:
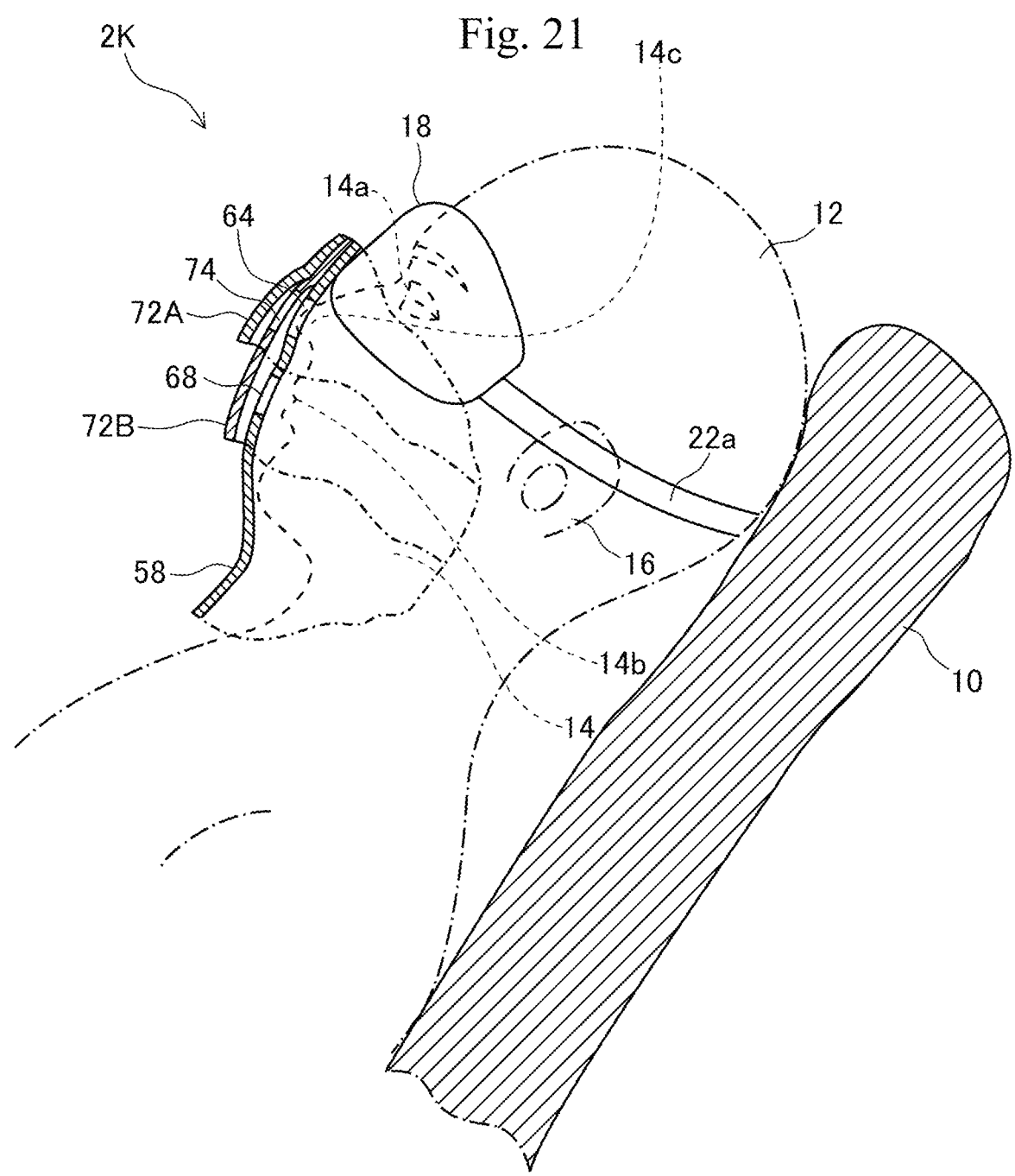
FIG. 21 A schematic cross-sectional view showing the usage state of the etiquette mask shown in FIG. 19, in the state without rolling up the covering cover.

FIG. 21 shows the use state of the etiquette mask 2K. The upper cover 72A is detachably attached to the upper mask part 18 by an unillustrated hook-and-loop fastener at its upper end. From the state shown in FIG. 21, when the upper cover 72A is rolled up, it becomes possible to inhale outside air with the nose 14c. The lower cover 72B includes an overlapping opening 74 that overlaps with the opening 64 corresponding to the nose part 14c. This prevents the opening function of the opening 64 for inhaling outside air through the nose 14c from being hindered, even if the lower cover 72B is not rolled up.

In addition, from the state where the upper cover 72A is rolled up, when the lower cover 72B is further rolled up, the opening 68 corresponding to the mouth part 14b is exposed to the outside, thereby becoming to a state that outside air can be inhaled by both of the mouth 14b and the nose 14c. If the user wants to inhale outside air with only the nose 14c, only the upper cover 72A needs to be rolled up, and if they want to inhale outside air with both the mouth 14b and the nose 14c, the lower cover 72B needs to be rolled up. Of course, it can also be used by rolling up the lower cover 72B to a halfway position where the opening 68 corresponding to the mouth part 14b is exposed to the outside. The vertical lengths of the upper cover 72A and the lower cover 72B on the face 14 may be made equal, and they may be configured to open and close individually.

Figure 22:
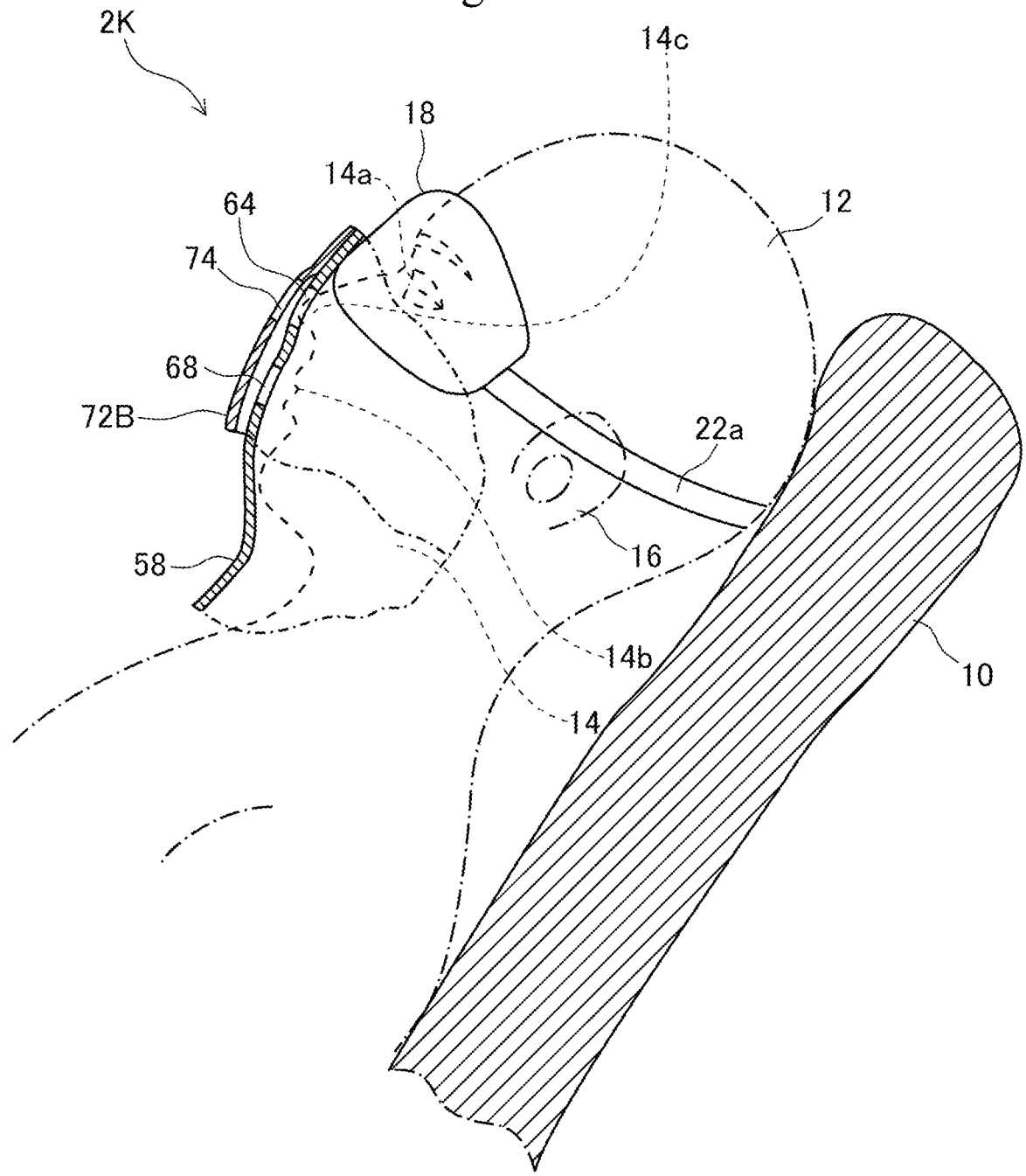
FIG. 22 A schematic cross-sectional view showing the usage state of the etiquette mask shown in FIG. 19, in the state with the upper cover removed.

As shown in FIG. 22, if one wants to continue to breathe outside air through the nose 14c, it may be configured such that the upper cover 72A can be removed from the upper mask part 18. Furthermore, the lower cover 72B may be attached and detached freely to the lower mask part 58 by a hook-and-loop fastener or the like, and the lower cover 72B may also be removed to maintain a state where outside air can be inhaled through the mouth 14b and the nose 14c. Furthermore, the lower mask part 58 may be attached and detached freely to the upper mask part 18 by a hook-and-loop fastener or the like, and the lower mask part 58 and the cover 72 may be collectively removed. Although not shown in the figure, if a band for attaching to the face is attached to the lower mask part 58 in advance, it is also possible to use the lower mask part 58 and the cover 72, which have been detached from the upper mask part 18, alone to put them on the face.

In the configurations of the eighth to eleventh embodiments, the configurations of the wearing part, upper mask part, and lower mask part of the first to seventh embodiments may be adopted as appropriate. As already described, the etiquette masks 2H to 2K of the eighth to eleventh embodiments have been described as not having ear plugs 9, but these etiquette masks 2H to 2K can carry ear plugs 90, which are separate parts, by keeping them in the pouch 76, which will be described later, as a storage bag.

Figure 23:
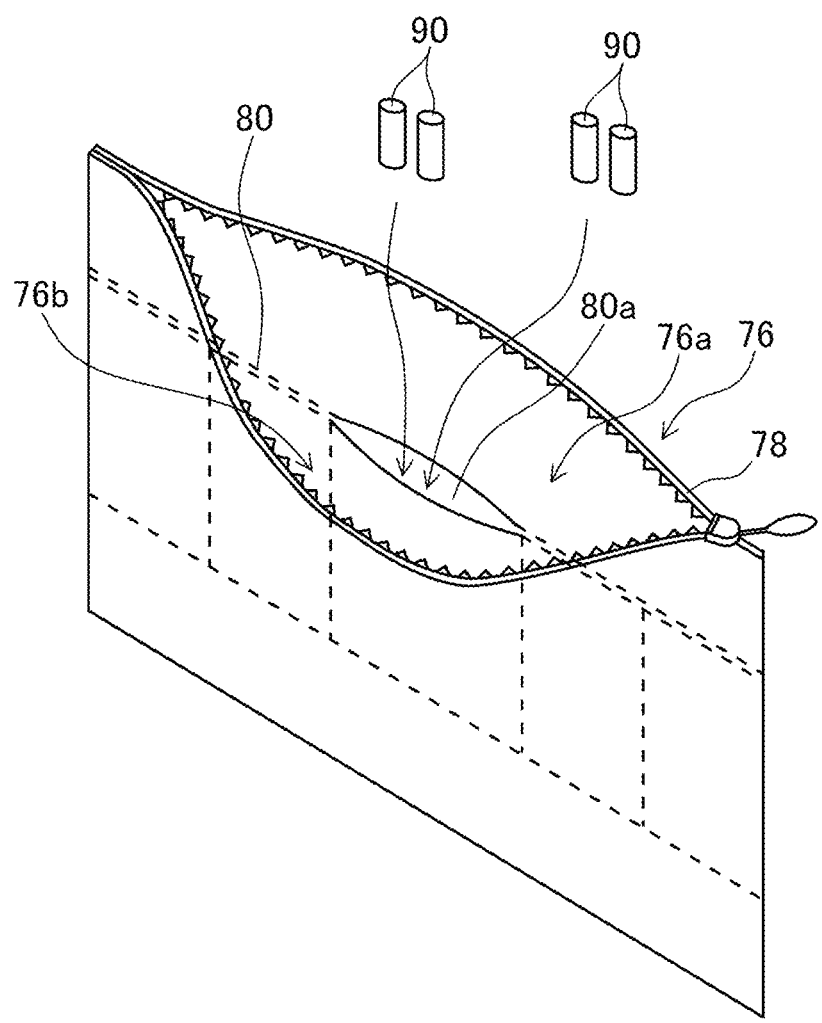
FIG. 23 An perspective view showing an example of a convenient pouch for carrying each etiquette masks according to the present embodiments.

FIG. 23 shows a pouch 76 which is convenient for carrying the etiquette mask (2H to 2K) according to particularly the eighth to eleventh embodiments. As shown in the figure, the pouch 76, which is opened and closed with a zipper 78, has a partition 80 inside and has storage parts 76a and 76b that can contain two etiquette masks separately. The partition 80 is made by overlapping two fabrics and sewing them together, and a pocket 80a for putting ear plugs 90 is formed in the central part. According to this pouch 76, since two different etiquette masks, such as those differing in color or configuration, can be folded, and stored, etiquette masks can be used properly according to the place and situation of use.

While the embodiments of the present invention have been described above, the present invention is not limited to these embodiments, and various modifications can be made within the scope of the claims and the technical ideas described in the specification and the drawings. For example, the fixation of the lower mask part to the upper mask part is not limited to sewing and it may be attached by snaps, buttons or the like, or by adhesives or the like, among others. The detachable structure of the lower mask part from the upper mask part shown in the second embodiment may be adopted in all embodiments. This detachable structure is not limited to a hook-and-loop fastener, and various ones such as snaps, buttons, and clips can be adopted. In the case of a detachable structure with a hook-and-loop fastener, depending on the type of fabric of the lower mask part, the fabric itself may be used so as to function as one of hook-and-loop fasteners by using pile or the like as the fabric itself. Although specific materials were exemplified for the upper mask part and the lower mask part in each of the above embodiments, various materials can be used without being limited thereto. The wearing portion, such as rubber bands and ear straps, may be provided on both the upper mask part and the lower mask part, and they may be used properly according to the situation. The position-adjustable rubber band 22 shown in the second embodiment can be adopted in place of the rubber band 8 in other embodiments. Also, the color of the lower mask part and the cover can be changed, or the design can be improved by applying a gradation of the same color series, etc.

The invention claimed is:

1. An etiquette mask comprising:
   an upper mask part that covers an eye region on a face;
   a lower mask part that covers a portion of the face below the eye region; and
   a rubber band provided on at least one of the upper mask part and the lower mask part to prevent falling off from the face,
   wherein the lower mask part has at least one opening at a position corresponding to the nose and at least one opening at a position corresponding to the mouth region on the face, and
   wherein a cover attached to either one of the upper mask part or the lower mask part can open and close the at least one opening,
   wherein the cover comprises an upper cover that covers an opening corresponding to the nose region and a lower cover that covers an opening corresponding to the mouth region,
   wherein the lower cover is longer than the upper cover in the vertical direction of the face, is arranged overlapping a lower surface of the upper cover, and overlaps the lower mask part corresponding to the mouth region,
   wherein the upper cover allows a user to lift the upper cover to obtain a fresh breath of air and then place the upper cover back down to cover the opening corresponding to the nose,
   wherein the lower cover allows a user to lift the lower cover to obtain a fresh breath of air and then place the lower cover back down to cover the opening corresponding to the mouth.

2. The etiquette mask according to claim 1, wherein the lower mask part has one opening that corresponds to both regions of the nose and mouth on the face.

3. The etiquette mask according to claim 1, wherein the cover is detachably attached to the lower mask part, or the lower mask part is detachably attached to the upper mask part.

4. The etiquette mask according to claim 1, wherein the lower mask part is formed of a soft fabric that deforms according to changes in the face's contours and has a bellows configuration that presents a curved shape protruding outward from the face when pulled in the vertical direction of the face.

* * * * *